United States Patent
Sakimoto et al.

(10) Patent No.: US 9,697,624 B2
(45) Date of Patent: Jul. 4, 2017

(54) IMAGE PROCESSING APPARATUS, RADIATION TOMOGRAPHY APPARATUS, AND METHOD OF PERFORMING IMAGE PROCESSING

(71) Applicant: Shimadzu Corporation, Kyoto-shi (JP)

(72) Inventors: Tomonori Sakimoto, Kyoto (JP); Kazuyoshi Nishino, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 162 days.

(21) Appl. No.: 14/470,985

(22) Filed: Aug. 28, 2014

(65) Prior Publication Data

US 2016/0063740 A1 Mar. 3, 2016

(51) Int. Cl.
- *G06K 9/00* (2006.01)
- *G06T 11/00* (2006.01)
- *G01N 23/04* (2006.01)

(52) U.S. Cl.
CPC .......... *G06T 11/005* (2013.01); *G01N 23/046* (2013.01); *G06T 2211/436* (2013.01)

(58) Field of Classification Search
None
See application file for complete search history.

(56) References Cited

U.S. PATENT DOCUMENTS

| | | | | |
|---|---|---|---|---|
| 6,307,909 B1 * | 10/2001 | Flohr | ................... | G01N 23/046 378/4 |
| 6,339,223 B1 * | 1/2002 | Motomura | ........... | A61B 6/5235 250/363.04 |
| 6,466,640 B1 * | 10/2002 | Taguchi | ................. | A61B 6/032 378/15 |
| 7,440,535 B2 * | 10/2008 | Netsch | .................. | G06T 11/005 378/4 |
| 7,660,379 B2 * | 2/2010 | Scholz | .................. | G06T 11/005 378/18 |
| 7,756,242 B2 * | 7/2010 | Kudo | ..................... | A61B 6/032 378/15 |
| 8,746,973 B2 * | 6/2014 | Gregerson | ............... | A61B 6/02 378/193 |

(Continued)

FOREIGN PATENT DOCUMENTS

WO    WO2011086604    7/2011

*Primary Examiner* — Matthew Bella
*Assistant Examiner* — Jose M Torres
(74) *Attorney, Agent, or Firm* — Muir Patent Law, PLLC

(57) ABSTRACT

An image processing apparatus and a radiation tomography apparatus capable of acquiring a tomographic image of high visibility are provided. The image processing apparatus initially generates a map m showing an extending direction of a linear structural object seen in an original image P0. Then, the apparatus generates an extrapolated image P1 by adding the area positioned at the side section of the original image P0 to the side section so as to extend the linear structural object seen in the side section by referring to the map m. By adding the side section to the original image P0 while shifting the pattern of the side section so as to extend the linear structural object seen in the side section of the image, the subject image can be naturally compensated. After this operation, by generating the tomographic image D, a tomographic image D having improved visibility can be generated.

20 Claims, 14 Drawing Sheets

(56) References Cited

U.S. PATENT DOCUMENTS

| | | | | |
|---|---|---|---|---|
| 2002/0154728 | A1* | 10/2002 | Morita | A61B 6/032 378/4 |
| 2002/0191737 | A1* | 12/2002 | Tanigawa | A61B 6/032 378/19 |
| 2004/0066876 | A1* | 4/2004 | Tam | A61B 6/032 378/4 |
| 2005/0111616 | A1* | 5/2005 | Li | A61B 6/025 378/22 |
| 2006/0222144 | A1* | 10/2006 | Russinger | H05G 1/38 378/16 |
| 2007/0064864 | A1* | 3/2007 | Wakai | A61B 6/032 378/4 |
| 2007/0110294 | A1* | 5/2007 | Schaap | G06K 9/40 382/131 |
| 2007/0230652 | A1* | 10/2007 | Scholz | G01N 23/046 378/4 |
| 2008/0123806 | A1* | 5/2008 | Scholz | G03B 42/026 378/18 |
| 2008/0219534 | A1* | 9/2008 | Faul | A61B 6/032 382/131 |
| 2009/0034817 | A1* | 2/2009 | Boese | A61B 6/4233 382/131 |
| 2011/0103662 | A1* | 5/2011 | Chiang | A61B 6/032 382/130 |
| 2012/0128119 | A1* | 5/2012 | Notohara | A61B 6/025 378/10 |
| 2013/0056644 | A1* | 3/2013 | Akahori | G06T 11/005 250/394 |
| 2013/0108007 | A1* | 5/2013 | Yin | A61B 6/032 378/4 |
| 2013/0216020 | A1* | 8/2013 | Notohara | A61B 6/02 378/22 |

* cited by examiner

Extrapolated transparent image ical institutions, as shown in FIG. 22, a radiographic apparatus 51 for acquiring a tomographic image of a subject may be used. In some radiographic apparatuses 51 of this kind, the apparatus is structured to acquire a tomographic image by superimposing a series of transparent images consecutively captured while synchronously moving a radiation source 53 for irradiating radiation and an FPD 54 for detecting the radiation. In such a radiographic apparatus 51, during the capturing of a series of transparent images, the radiation source 53 and the FPD 54 move so as to approach with each other in a body axis direction of the subject. After the position of the radiation source 53 and that of the FPD 54 in the body axis direction coincide, the radiation source 53 and the FPD 54 move so as to distance themselves with respect to each other in the body axis direction. Such a radiographic apparatus is disclosed, for example, in Patent Document 1 (see. e.g., International Publication No. WO2011/086604).

IMAGE PROCESSING APPARATUS, RADIATION TOMOGRAPHY APPARATUS, AND METHOD OF PERFORMING IMAGE PROCESSING

BACKGROUND OF THE INVENTION

Field of the Invention

The present disclosure relates to an image processing apparatus, and more specifically to an image processing apparatus that acquires a tomographic image of a subject based on a series of transparent images captured while synchronously moving a radiation source and a FPD (flat panel-type X-ray detector) in opposite directions with each other, and also relates to a radiation tomography apparatus equipped with the image processing apparatus and a method of performing image processing.

Description of the Related Art

The following description of related art sets forth the inventors' knowledge of related art and certain problems therein and should not be construed as an admission of knowledge in the prior art.

In medical institutions, as shown in FIG. 22, a radiographic apparatus 51 for acquiring a tomographic image of a subject may be used. In some radiographic apparatuses 51 of this kind, the apparatus is structured to acquire a tomographic image by superimposing a series of transparent images consecutively captured while synchronously moving a radiation source 53 for irradiating radiation and an FPD 54 for detecting the radiation. In such a radiographic apparatus 51, during the capturing of a series of transparent images, the radiation source 53 and the FPD 54 move so as to approach with each other in a body axis direction of the subject. After the position of the radiation source 53 and that of the FPD 54 in the body axis direction coincide, the radiation source 53 and the FPD 54 move so as to distance themselves with respect to each other in the body axis direction. Such a radiographic apparatus is disclosed, for example, in Patent Document 1 (see. e.g., International Publication No. WO2011/086604).

The operation of capturing a tomographic image mentioned above by the radiographic apparatus 51 will be explained. Initially, the radiation source 53 irradiates radiation intermittently while moving. For example, every time one irradiation is completed, the radiation source 53 moves in the body axis direction of the subject and again irradiates radiation. Thus, a total number of pieces of transparent images (e.g., 74) are acquired, and superimposed. The completed image is a tomographic image in which a tomogram acquired by cutting the subject at a certain cutting plane is seen.

However, conventional technologies as mentioned above have certain problems. For example, in the conventional radiographic apparatus 51, disturbance of images often occurs at the end sections of the tomographic image.

A transparent image is acquired while moving the X-ray tube 53 and the FPD 54 with respect to the object, and therefore the position where the subject is seen differs in each transparent image. Accordingly, the image of the subject seen in an end section of a certain transparent image is not seen in another transparent image. However, such a situation will not be considered at the time of generating a tomographic image D. For example, a tomographic image D is generated on the assumption that images of the subject required for reconstruction are all contained in the transparent image.

Then, at the end section of the tomographic image D to be generated, an image of the subject that may be required to generate a tomographic image D may be missing. Such lacking of an image shows up as a false image in a tomographic image D. More concretely, as shown in FIG. 23, the image may be disturbed notably at both sections of the tomographic image D in the moving direction of the FPD 54 and the radiation source 53.

Under the circumstances, in a conventional structure, by compensating the lack of images to generate a tomographic image, attempts may be made to enhance the visibility of the tomographic image. One method is to compensate for the lack of images by extending the transparent image by repeatedly pasting the pattern of the end section of the transparent image. However, it cannot be said that sufficient image extrapolation is performed in this method. In detail, in the aforementioned method, since an end section of the image is simply pasted without considering the image of the subject to be seen in the image, as shown in FIG. 24, joined images of the subject may become discontinuous. Thus, in some cases, the end section of the image becomes more unnatural by the extrapolation processing. Under the circumstances, in a conventional method, the visibility of the tomographic image may deteriorate more than generating a tomographic image without performing extrapolation.

The description herein of advantages and disadvantages of various features, embodiments, methods, and apparatus disclosed in other publications is in no way intended to limit the present invention. For example, certain features of the described embodiments of the invention may be capable of overcoming certain disadvantages and/or providing certain advantages, such as, e.g., disadvantages and/or advantages discussed herein, while retaining some or all of the features, embodiments, methods, and apparatus disclosed therein.

SUMMARY OF THE INVENTION

The disclosed embodiments of the present invention have been developed in view of the above-mentioned and/or other problems in the related art. The disclosed embodiments of the present invention can improve upon existing methods and/or apparatuses.

The embodiments of the present invention have been made in view of the aforementioned circumstances, and aim to provide an image processing apparatus that acquires a tomographic image from a plurality of transparent images capable of acquiring a tomographic image excellent in visibility.

Some embodiments of the present invention have the following structure. For example, the image processing apparatus may include a map generation block, an extrapolation block, and a tomographic image generation block. In certain embodiments, the map generation section is configured to generate a gradient vector map by calculating gradient vectors showing an extending direction of a linear structural object seen in an image and arranging the vectors. The extrapolation section is configured to generate an extrapolated image by adding a duplicate of an area positioned at a side section of the image to the side section of the image so that the linear structural object seen in the side section of the image is arranged in the extending direction of the linear structural object. The tomographic image generation section is configured to generate a tomographic image by superimposing extrapolated images generated based on a series of images consecutively acquired while moving a radiation source for irradiating an X-ray to a subject and a radiation detection section for detecting the X-ray passed through the subject synchronously in opposite directions. The extrapolation section performs image processing to both end sections of the image in a direction in which the radiation source and the radiation detection section move.

In one embodiment, the image processing apparatus initially generates a gradient vector map showing an extending direction of a linear structural object seen in an image. Then, the image processing apparatus generates an extrapolated image by adding a duplicate of an area positioned at a side section of the image to the side section of the image so that the linear structural object seen in the side section of the original image is arranged in the extension direction of the linear structural object. Further, this adding operation may be performed to both ends of the image in the moving direction of the radiation source and the radiation detection means. As explained above, both ends of the image in the moving direction may be added so as to extend the linear structural object, and an extrapolated image may be generated. Since the portion deviated from the side section of the image may be a portion where no image could be acquired, there may not be any means to actually know the state of the transparent image. However, it is assumed that the image of the subject at the portion deviated from the image will continue for a while at least in the same pattern that the image of the side section of the image is extended.

Therefore, by adding the pattern of the side section of the image to the image while shifting the pattern in the extending direction of the side section so that the linear structural object seen in the side section of the image is extended, it becomes possible to extrapolate the portion where no image could be acquired more naturally.

Further, it is may be desirable that in the image processing apparatus, the extrapolation section operates to duplicate a strip-like pixel array positioned at the side section extending in the orthogonal direction perpendicular to the moving direction in the original image P0 and add the duplicate to the side section.

The aforementioned structure shows a concrete structure of the extrapolation section. For example, when the extrapolation section operates to duplicate a strip-like pixel array positioned at the side section extending in the orthogonal direction perpendicular to the moving direction, it is possible to generate an extrapolated image more assuredly. Further, in the aforementioned image processing apparatus, it may be desirable that the extrapolation section performs smoothing processing of the strip-like pixel array in the orthogonal direction when adding a pixel.

The aforementioned structure shows a concrete structure of the extrapolation section. For example, at the time of adding pixels, when the extrapolation section performs smoothing processing to the strip-like pixel array in the orthogonal direction, a more clear tomographic image can be obtained. It is predicted that a transparent image of the subject positioned outside the image is almost the same as the subject image seen in the side section. However, in reality, the transparent image of the subject positioned outside the image and the subject image seen in the side section of the image are not exactly same. Therefore, if the pixel is added as it is, a pattern different from the actual pattern will be added to the original image P0, resulting in an unnatural tomographic image D. According to the aforementioned structure, since smoothing processing is performed and then pixels are added, unnaturalness of the tomographic image becomes less noticeable, and the visibility of the tomographic image D improves. Further, in the aforementioned image processing apparatus, it is desirable that the extrapolation section gradually enhances the degree of blurring of smoothing processing to be performed to the pixel array to be added as the operation for adding a plurality of pixel arrays repeats.

The aforementioned structure shows a concrete structure of the extrapolation section. The prediction of the subject image not seen in the original image P0 becomes difficult as the predicting portion of the subject image deviates from the side section of the image. For example, in the outside area of the image, the transparent image of the subject adjacent to the side section of the original image P0 is almost the same as the subject image seen in the side section. However, in the outside area of the image, the image of the subject becomes different from the subject image seen in the side section. According to some embodiments of the present invention, the degree of blurring of the smoothing processing to be performed to the pixel array to be added is gradually enhanced as the operation of adding a plurality of pixel arrays repeats. With this, as the adding operation is repeated, it becomes possible to avoid the possibility that patterns which gradually differ from the original subject image are added.

Further, in the radiation tomography apparatus mounting the aforementioned image processing apparatus, it is desirable to provide a radiation source that irradiates radiation to a subject, a radiation detection section for detecting the radiation passed through the subject, a moving mechanism for moving the radiation source and the radiation detection section synchronously in a moving direction in opposite directions with respect to the subject, a movement control section for controlling the moving mechanism, and an image generation section for generating an image based on an output of the radiation detection section.

The aforementioned structure shows a structure of a radiation tomography apparatus mounting the image processing apparatus. According to the radiation tomography apparatus according to some embodiments of the present invention, a tomographic image improved in visibility of both ends of the tomographic image can be obtained.

In one embodiment, the image processing apparatus initially generates a gradient vector map m showing an extending direction of a linear structural object seen in an image. Then, the image processing apparatus generates an extrapolated image by adding the duplicate of the area positioned at the side section of the image to the side section of the image so that the linear structural object seen in the side section of the image is arranged in the extension direction of the linear structural object. By adding the side section to the image while shifting the pattern of the side section so as to extend the linear structural object seen in the side section of the image, the subject image can be naturally compensated. After this operation, by generating a tomographic image, a tomographic image excellent in visibility can be generated.

In one embodiment, an image processing apparatus includes: map generation means for generating a gradient vector map by calculating gradient vectors showing an extending direction of a linear structural object seen in an image and arranging the vectors; extrapolation means for generating an extrapolated image by adding a duplicate of an area of the image positioned at a side section of the image to the side section of the image so that the linear structural object seen in the side section of the image is arranged in the extending direction of the linear structural object; and tomographic image generation means for generating a tomographic image by superimposing extrapolated images generated based on a series of images consecutively acquired while moving a radiation source for irradiating an X-ray to a subject and a radiation detection means for detecting the X-ray passed through the subject synchronously in opposite directions. The extrapolation means are configured to perform image processing on both end sections of the image in a direction in which the radiation source and the radiation detection means move.

In another embodiment, a method of performing image processing includes: generating a gradient vector map by calculating gradient vectors showing an extending direction of a linear structural object seen in an image and arranging the vectors; generating an extrapolated image by adding a duplicate of an area of the image positioned at a side section of the image to the side section of the image so that the linear structural object seen in the side section of the image is arranged in the extending direction of the linear structural object; and generating a tomographic image by superimposing extrapolated images generated based on a series of images consecutively acquired while moving a radiation source for irradiating an X-ray to a subject and a radiation detection means for detecting the X-ray passed through the subject synchronously in opposite directions. Image processing is performed on both end sections of the image in a direction in which the radiation source and the radiation detection means move.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims. In the drawings, the size and relative sizes of layers and regions may be exaggerated for clarity. Like numbers refer to like elements throughout. The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/". It will be understood that, although the terms first, second, etc. may be used herein to describe various elements, these elements should not be limited by these terms. Unless indicated otherwise, these terms are only used to distinguish one element from another. For example, a first object could be termed a second object, and, similarly, a second object could be termed a first object without departing from the teachings of the disclosure. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise. Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

BRIEF DESCRIPTION OF THE DRAWINGS

The disclosed embodiments of the present invention are shown by way of example, and not limitation, in the accompanying figures.

DETAILED DESCRIPTION

In the following paragraphs, some embodiments of the invention will be described by way of example and not limitation. It should be understood based on this disclosure that various other modifications can be made by those in the art based on these illustrated embodiments.

Example 1

Figure 1:
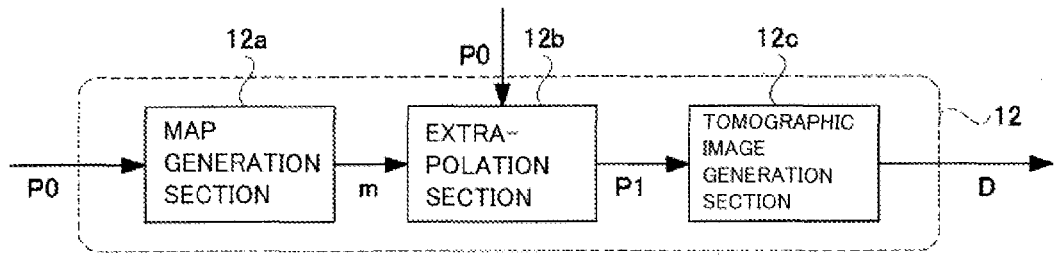
FIG. 1 is a functional block diagram for explaining a structure of an image processing apparatus according to one exemplary embodiment.

As shown in FIG. 1, in the image processing apparatus according to Example 1, it is configured such that, when an image acquired by photographing a subject with an X-ray (hereinafter referred to as "original image P0") is input, a tomographic image D of the subject cut at a cutting plane is output. The original image P0 corresponds to an image as defined by the present disclosure.

(Entire Structure of Image Processing Apparatus)

As shown in FIG. 1, the image processing apparatus 12 according to Example 1 includes a map generation section 12a, an extrapolation section 12b, and a tomographic image generation section 12c. The map generation section 12a is configured to calculate gradient vectors showing an extending direction of a linear structural object seen in the original image P0 and arrange them to generate a gradient vector map (hereinafter simply referred to as map "m"). An extrapolation section 12b is configured to generate an extrapolated image P1 by adding an area positioned at a side portion of the original image P0 while displacing it in an extending direction of the side portion so as to extend the linear structural object seen in the side portion of the original image P0 while referring to the map "m." A tomographic image generation section 12c is configured to generate a tomographic image D by superimposing extrapolated images P1 generated based on a series of original images P0 consecutively acquired while moving the X-ray tube for irradiating an X-ray to a subject and the FPD 4 for detecting the X-ray passed through the subject synchronously in opposite directions along a moving direction. The operation of each section will be explained later. The X-ray tube 3 corresponds to a radiation source of the present disclosed embodiments, and the FPD 4 corresponds to a radiation detection means of the present disclosed embodiments. Further, the map generation section 12a, also described as a map generation block 12a, corresponds to an image generation means of the present disclosed embodiments, and the extrapolation section 12b, also described as an extrapolation block 12b, corresponds to an extrapolation means of the present disclosed embodiments. And, the tomographic image generation section 12c, also described as a tomographic image generation block 12c, corresponds to a tomographic image generation means of the present invention, and the map "m" corresponds to a gradient vector map. The various "sections" or "blocks" described herein may be implemented as devices formed of different elements configured to perform the described actions. For example, one of the blocks, such as the map generation section 12a, may be formed of a combination of hardware with software and/or firmware. A block may be configured to perform certain actions by using or programming different circuitry, hardware, software, firmware, or combinations thereof. Other of the blocks may be formed similarly, and certain sections may be physically combined, for example, to be implemented with the same hardware and/or firmware, having different software programs or algorithms to perform different tasks. In general, the map generation block 12a, extrapolation block 12b, tomographic image generation block 12c, and other elements of image processing apparatus 12 may be comprised of one or more processors or computers configured by software. Other elements of X-ray equipment 1, described further below, such as a main controller 25, console, 26, display 27, and storage 23 may constitute elements of such computer(s). A "computer" refers to one or more apparatus and/or one or more systems that are capable of accepting a structured input, processing the structured input according to prescribed rules, and producing results of the processing as output. Examples of a computer may include: a general purpose computer; a stationary and/or portable computer; a computer having a single processor, multiple processors, or multi-core processors, which may operate in parallel and/or not in parallel; a supercomputer; a mainframe; a super mini-computer; a mini-computer; a workstation; a micro-computer; a server; a client; a web appliance; a telecommunications device with internet access; a tablet personal computer (PC); a personal digital assistant (PDA); application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC). "Software" refers to prescribed rules to operate a computer. Examples of software may include: code segments; instructions; applets; pre-compiled code; compiled code; interpreted code; computer programs; and programmed logic. A computer as described herein may include software in order to perform particular actions.

<Structure of X-Ray Tomographic Apparatus>

Figure 2:
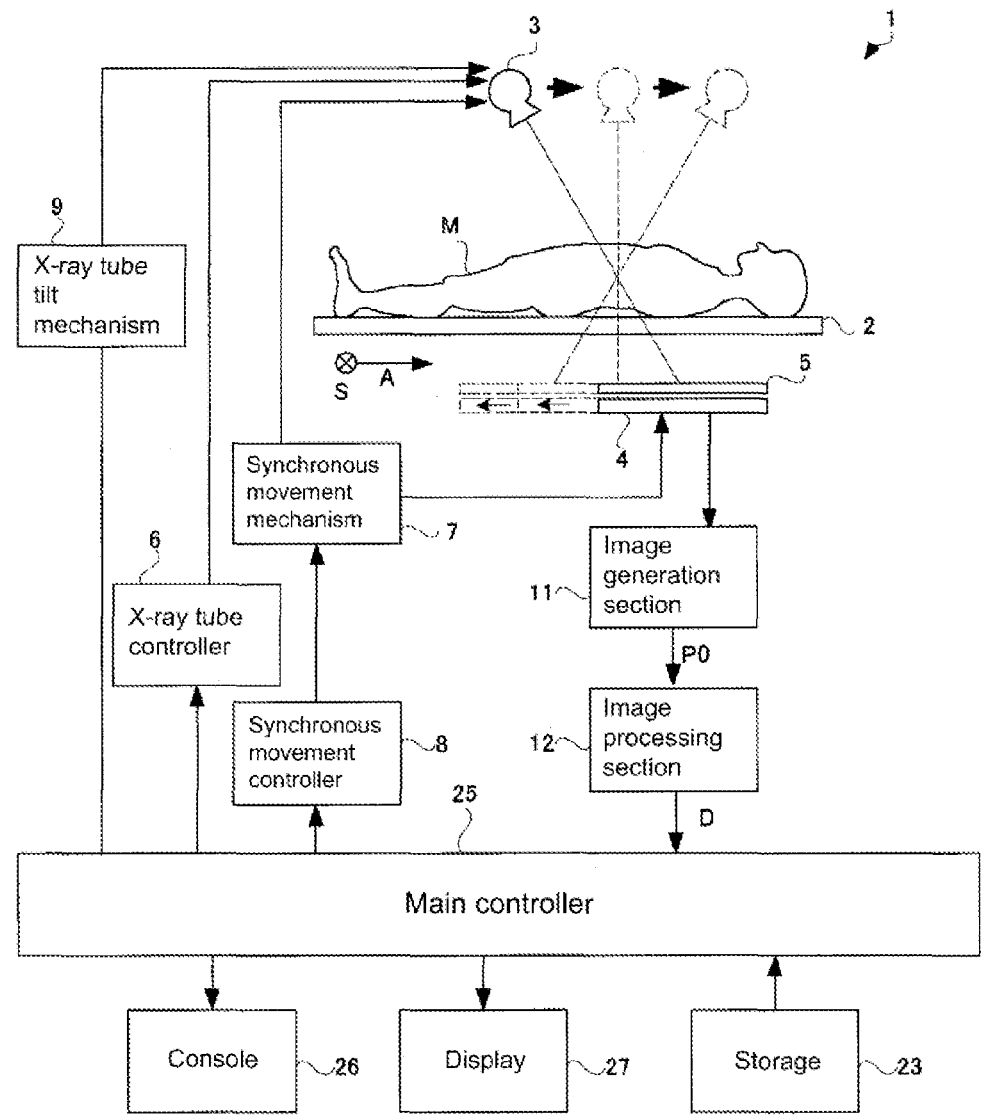
FIG. 2 is a functional block diagram for explaining a structure of an X-ray tomographic apparatus according to one exemplary embodiment.

FIG. 2 is a functional block diagram for explaining a structure of a radiation tomographic apparatus according to Example 1. As shown in FIG. 2, the X-ray equipment 1 is provided with a top board 2, an X-ray tube 3, a flat-panel type X-ray detector 4 (hereinafter referred to as "FPD"), a synchronous movement mechanism 7, a synchronous movement controller 8, and an X-ray grid 5. The top board 2 is configured to support a subject M which is an object of an X-ray tomography. The X-ray tube 3 is configured to irradiate a cone-shaped X-ray beam to the subject M arranged on the upper portion of the top board 2 (one surface side of the top board 2). The sheet-like flat panel type X-ray detector 4 (FPD) is arranged below the top board 2 (on the other surface side of the top board) to detect the X-ray passed through the subject M. The synchronous movement mechanism 7 is configured to move the X-ray tube 3 and the FPD 4 synchronously in opposite directions with respect to the part of interest of the subject M in a state in which, in one embodiment, the central axis of the cone-shaped X-ray beam and the central point of the FPD 4 always coincide. The synchronous movement controller 8 controls the synchronous movement mechanism 7. The X-ray grid 5 is arranged so as to cover the X-ray detection plane for detecting the X-ray of the FPD 4 to absorb the scattered X-rays. As explained above, the top board 2 is arranged at the position between the X-ray tube 3 and the FPD 4. The X-ray tube 3 corresponds to a radiation source of the present disclosed embodiments, and the FPD 4 corresponds to a radiation detector of the present disclosed embodiments. Further, the synchronous movement controller 8 corresponds to a movement controller of the present disclosed embodiments, and the synchronous movement mechanism 7 corresponds to a moving mechanism of the present disclosed embodiments.

The X-ray tube 3 is configured to repeatedly irradiate a cone-shaped pulsed X-ray beam to the subject M in accordance with the control of the X-ray tube controller 6. The X-ray tube 3 is equipped with a collimator that collimates the X-ray beam into a pyramid cone-shape. The X-ray tube 3 and the FPD 4 constitute an imaging system 3 and 4 for capturing an X-ray transparent image.

The synchronous movement mechanism 7 is configured to synchronously move the X-ray tube 3 and the FPD 4. This synchronous movement mechanism 7 moves the X-ray tube 3 straight along the straight line orbit (in the longitudinal direction of the top board 2) parallel to the body axis direction A of the subject M in accordance with the control of the synchronous movement controller 8. The moving directions of the X-ray tube 3 and the FPD 4 coincide with the longitudinal direction of the top board 2. Further, during the examination, the cone-shaped X-ray beam irradiated from the X-ray tube 3 is always pointed to the part of interest of the subject M, and the X-ray irradiation angle can be changed, for example, from an initial angle of −20° to a final angle of +20° by changing the angle of the X-ray tube 3. Such X-ray irradiation angle change is performed by an X-ray tube tilt mechanism 9.

Further, the synchronous movement mechanism 7 moves the FPD 4 arranged below the top board 2 straight in the body axis direction A of the subject M (in the longitudinal direction of the top board 2) in synchronization with the straight movement of the aforementioned X-ray tube 3. The moving direction is opposite to the moving direction of the X-ray tube 3. In detail, it is structured such that the cone-shaped X-ray beam in which the irradiation source position and the irradiation direction change due to the movement of the X-ray tube 3 is always received by the entire surface of the X-ray detection plane of the FPD 4. As explained above, during a single examination, the FPD 4 acquires a total of, for example, 74 pieces of original images P0 while moving in synchronization with the X-ray tube 3 in a direction opposite to the moving direction of the X-ray tube 3. Specifically, the imaging system 3 and 4 moves from the initial position shown by an actual line to the position shown by an alternate long and short dash line via the position shown by a broken line as shown in FIG. 2. Thus, a plurality of X-ray transparent images are acquired while changing the position of the X-ray tube 3 and that of the FPD 4. In one embodiment, the cone-shaped X-ray beam is always received by the entire surface of the X-ray detection plane of the FPD 4, and therefore the central axis of the cone-shaped X-ray beam always coincides with the center point of the FPD 4 during the image acquiring operation. Further, during the image acquiring operation, although the center of the FPD 4 moves straight, the direction of the movement is opposite to the direction of the movement of the X-ray tube 3. As such, it is structured such that the X-ray tube 3 and the FPD 4 are synchronously moved along the body axis direction A in opposite directions with each other.

Next, a collimator provided at the X-ray equipment 1 will be explained. The collimator is mounted on the X-ray tube 3 to collimate the X-ray irradiated from the X-ray tube 3 into an X-ray beam 19 of a four pyramid shape (cone-shape).

Figure 3:
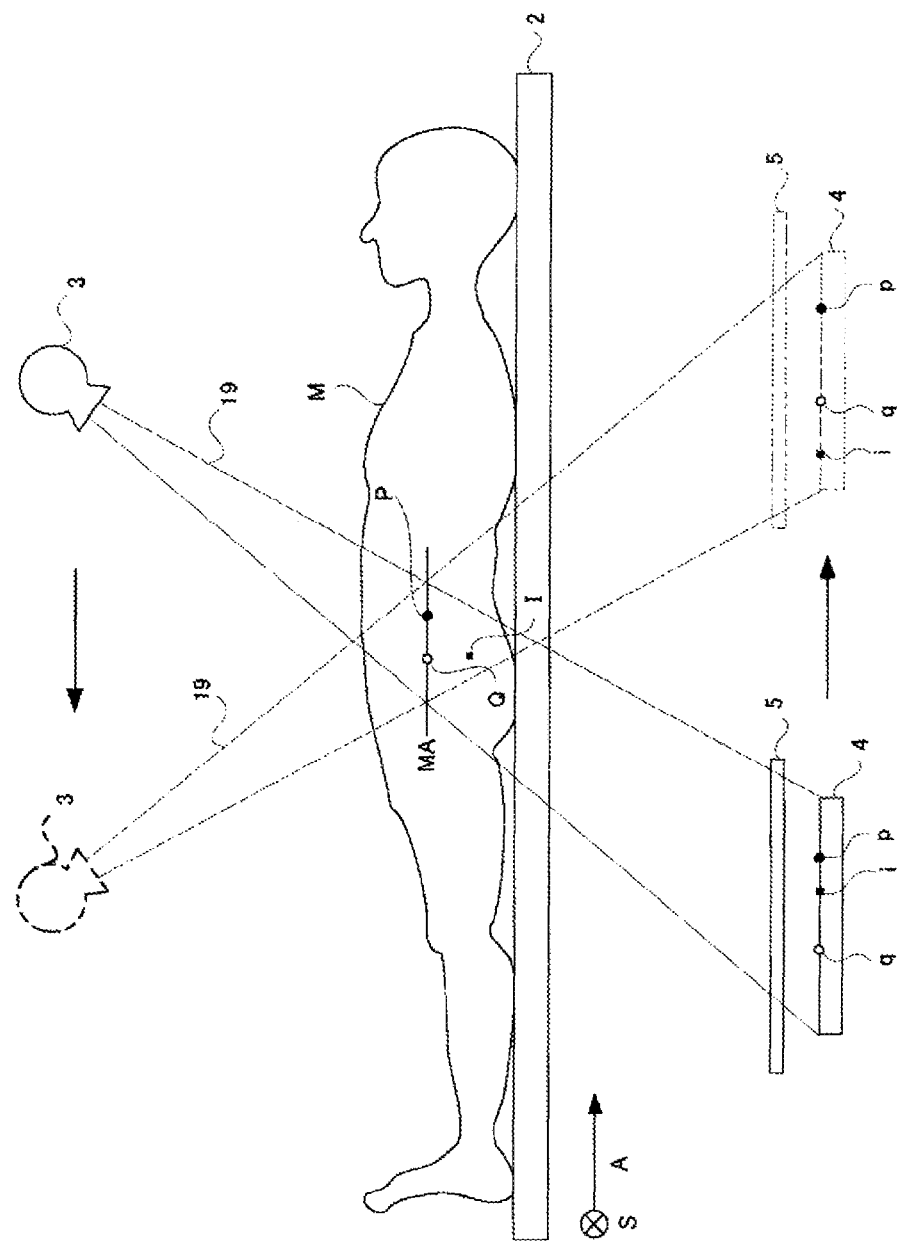
FIG. 3 is a schematic view for explaining a principal of tomography according to one exemplary embodiment.

Next, the principle of acquisition of tomographic images in the X-ray equipment 1 according to Example 1 will be explained. FIG. 3 is a view for explaining the acquisition method of a tomographic image in the X-ray equipment 1 according to one exemplary embodiment. For example, the explanation will be directed to a reference cutting plane MA arranged in parallel with the top board 2 (arranged horizontally with respect to the vertical direction). As shown in FIG. 3, a series of original images P0 are generated in the image generation section 11 while moving the FPD 4 in a direction opposite to the moving direction of the X-ray tube 3 in line with the irradiation direction of the cone-shaped X-ray beam 19 by the X-ray tube 3 so that the points P and Q positioned in the reference cutting plane MA are always projected to the fixed points p and q on the X-ray detection plane, respectively. In the series of original images P0, the projection image of the subject is seen while changing its position. By superimposing the series of original images P0 (correctly, the extrapolated images P1 to which the below-mentioned extrapolation processing was executed) at the image processing section (image processing apparatus such as an image processor) 12, the images (e.g., fixed points p, q) positioned in the reference cutting plane MA are integrated, enabling imaging as an X-ray tomographic image. On the other hand, the point I not positioned in the reference cutting plane MA is seen as a point i in each of the series of subject images while changing its projection position on the FPD 4. Such point i, different from the fixed points p and q, does not focus into an image at the time of superimposing the X-ray transparent images at the image processing section 12 and blurs. As explained above, by superimposing the series of original images P0 (extrapolated images P1), an X-ray tomographic image in which only the image positioned at the reference cutting plane MA of the subject M is seen can be obtained. As explained above, when the X-ray transparent images are simply superimposed, an X-ray tomographic image at the reference cutting plane MA can be obtained. The vertical position of the reference cutting plane MA is the reference cutting position described herein. The image generation section 11 corresponds to an image generation means as described herein.

Further, by changing the setting of the image processing section 12, even at any arbitrary cutting position horizontal to the reference cutting plane MA, a similar tomographic image can be obtained. During the image acquisition processing, although the projection position of the aforementioned point i moves on the FPD 4, the moving speed increases as the distance between the point I before the projection and the reference cutting plane MA increases. Utilizing it, by superimposing the series of subject images obtained while shifting in the body axis direction A at a predetermined pitch, an X-ray tomographic image at a cutting position parallel to the reference cutting plane MA can be obtained. Superimposing the series of subject images mentioned above is performed by the image processing section 12. The method of acquiring a tomographic image as explained above is referred to as a filter back projection.

Comparing the original images P0 acquired while moving the imaging system 3 and 4, the image of the subject M is seen in the original image P0 while shifting in the moving direction of the imaging system 3 and 4. This is because the shape of the projection of the subject M to be projected on the FPD 4 changes as the position of the imaging system 3 and 4 changes in the moving direction. On the other hand, the shape of a leaf seen in the series of original images P0 do not follow the shift of the image of the subject M, and comes out in every original images P0 in the same manner.

Figure 4:
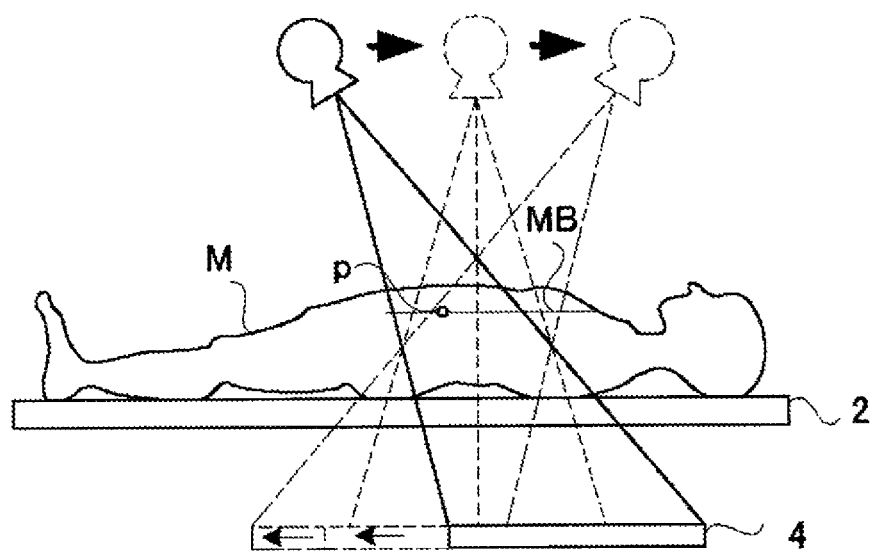
FIG. 4 is a schematic view for explaining a state in which a subject is imaged in an original image in the X-ray tomographic apparatus according to one exemplary embodiment.

Hypothetically speaking, if it is tried to acquire a tomographic image D using original images P0 as they are, especially at both end sections of the tomographic image D in the lengthwise direction (in the direction corresponding to the moving direction of the imaging system 3 and 4), the tomographic image of the subject M will be disturbed. The principle of disturbance of the tomographic image will be explained. In this embodiment, a tomographic image of the subject M at the cutting surface MB including the point p in the subject M as shown in FIG. 4 will be generated. From FIG. 4, it is understood that the position where the point p is seen on the FPD 4 moves gradually toward the end of the FPD 4 in accordance with the movement of the imaging system 3 and 4. In detail, when the imaging system 3 and 4 is positioned as shown by the solid line, the point p is positioned at the central part of the X-ray beam, and when the imaging system 3 and 4 is moved to the position shown by the alternate long and short dash line, the point p is positioned at the end portion of the X-ray beam.

Figure 5:
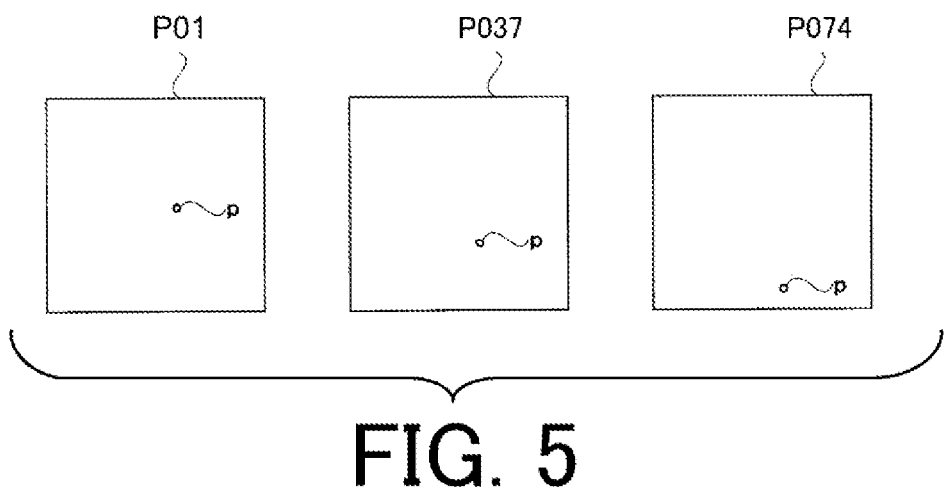
FIG. 5 is a schematic view for explaining a state in which a subject is imaged in an original image in the X-ray tomographic apparatus according to one exemplary embodiment.

The schematic view showing how the point p is seen in 74 pieces of original images P0 is shown in FIG. 5. The original image P01 in FIG. 5 shows an image acquired at the 1$^{st}$ image acquisition processing, which is an image acquired when the imaging system 3 and 4 in FIG. 4 is in the position shown by the solid line. The original image P037 in FIG. 5 shows an image acquired at the 37$^{th}$ image acquisition processing, which is an image acquired when the imaging system 3 and 4 in FIG. 4 is in the position shown by the broken line. Further, the original image P074 in FIG. 5 shows an image acquired at the 74$^{th}$ image acquisition processing, which is an image acquired when the imaging system 3 and 4 in FIG. 4 is in the position shown by the alternate long and short dash line. As will be understood by comparing each image, when comparing the original images P0 in the order of acquisition, the point p is moved toward the lower end of the original image P0. The point p is seen in all of the original images P0 while changing its position.

Figure 6:
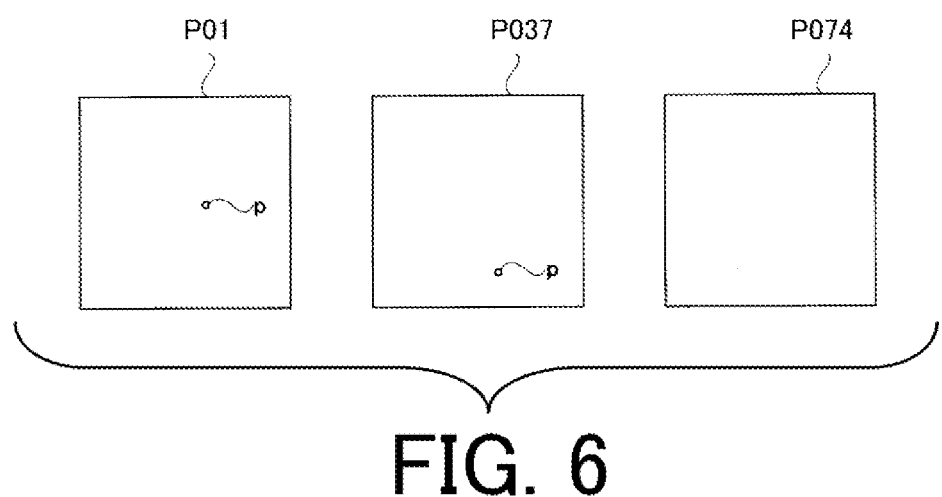
FIG. 6 is a schematic view for explaining a state in which a subject is imaged in an original image in the X-ray tomographic apparatus according to one exemplary embodiment.

The explanation using FIG. 5 is based on an ideal original image P0. Actually, however, as shown in FIG. 6, the point p is not always seen in all of the original images P0. That is, a part of the image of the subject M which is supposed to be seen in the peripheral edge of each original image P0 deviates from the photographing visual field as the X-ray tube 3 and the FPD 4 move. As for the point p, as original images P0 are consecutively acquired, the point p moves toward the lower end side of the original image P0 and finally deviates from the photographing visual field. Thus, the point p is not seen in all of the original images P0.

If it is attempted to focus the point p on the tomographic image D using the original images P0 as shown in FIG. 6, images to be added become insufficient. As a result, the pixel level of the point p becomes extremely dark. Such a disturbance of the tomographic image D is extremely notable at the upper end section and the lower end section of the tomographic image D when the direction corresponding to the moving direction of the imaging system 3 and 4 is defined as a lengthwise direction. The reason is that the image of the subject to be seen at the end section of the tomographic image D readily deviates from the photographing visual field in accordance with the movement of the imaging system 3 and 4.

Figure 7:
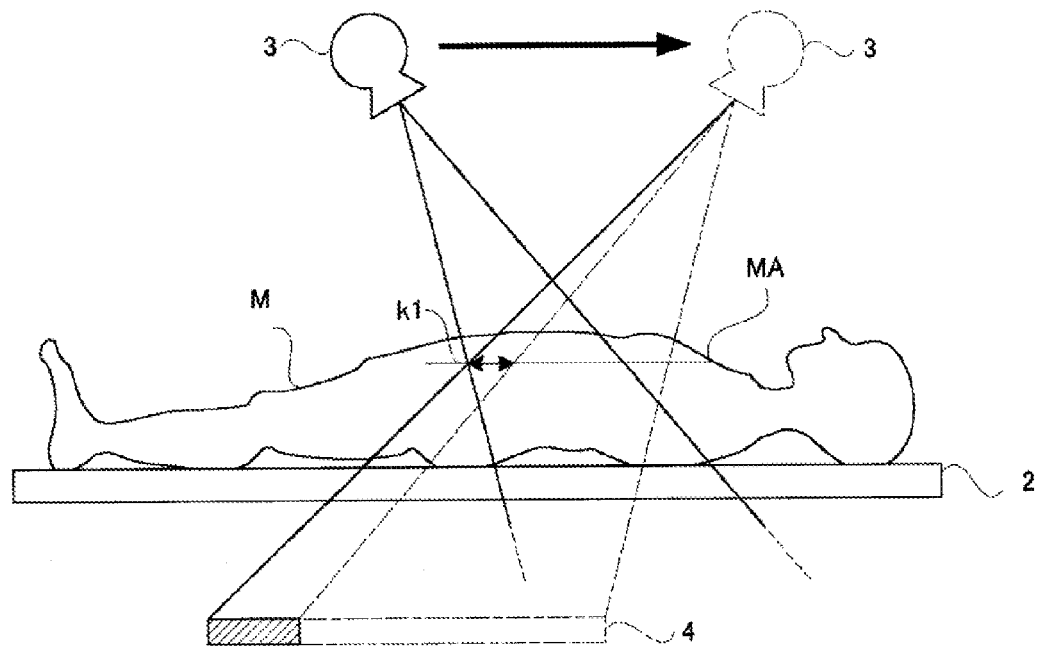
FIG. 7 is a schematic view for explaining a state in which a subject is imaged in an original image in the X-ray tomographic apparatus according to one exemplary embodiment.

FIG. 7 shows a comparison of positions where the subject M is to be seen between the initially acquired original image and the lastly acquired original image among consecutively acquired original images P0. In FIG. 7, the position of the X-ray tube 3 at the initial photographing is shown by a solid line, and the position of the X-ray tube 3 at the last photographing is shown by a dashed line. The subject image on the reference cutting plane MA shown by the arrow in FIG. 7 is seen in the initially acquired original image, but not in the last acquired original image P0. Such shortage of the subject image causes disturbance of the tomographic image D. Here, the position of one of end portions of the X-ray beam on the reference cutting plane MA on a direction side opposite to the moving direction of the X-ray tube 3 when the X-ray beam is irradiated from the X-ray tube 3 in the consecutive photographing start position is defined as a start side reference position k1.

Figure 8:
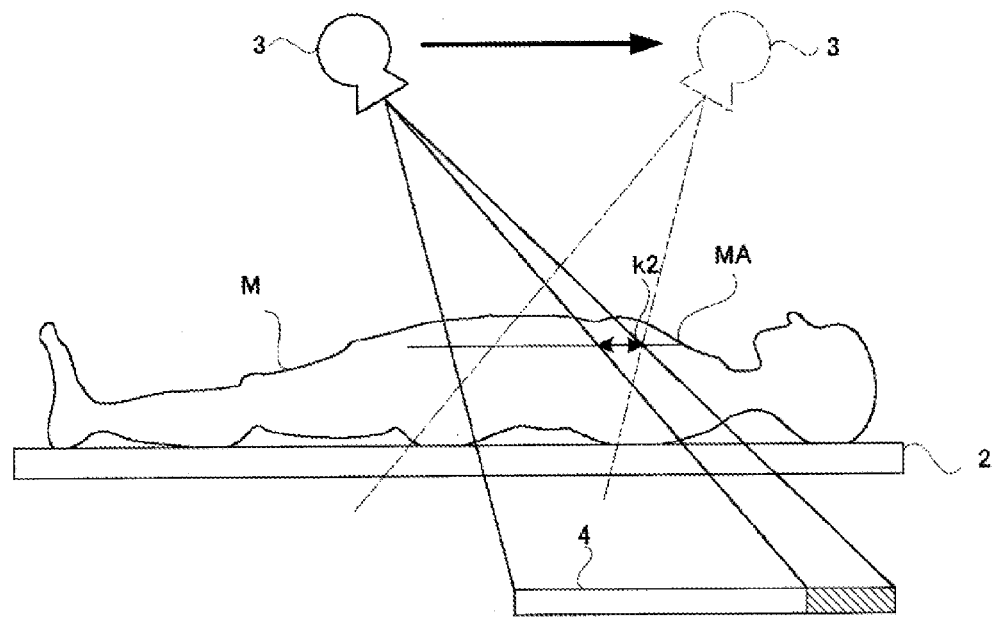
FIG. 8 is a schematic view for explaining a state in which a subject is imaged in an original image in the X-ray tomographic apparatus according to one exemplary embodiment.

FIG. 8 also shows the comparison of the position where the subject M is seen on the initially acquired original image P0 and the position where the subject M is seen on the lastly acquired original image P0. In FIG. 8, the position of the X-ray tube 3 at the initial photographing is shown by a solid line, and the position of the X-ray tube 3 at the last photographing is shown by a dashed line. The subject image on the reference cutting plane MA shown by the arrow in FIG. 8 is seen in the initially acquired original image, but not in the last acquired original image P0. Such shortage of the subject image also causes disturbance of the tomographic image D. Here, the position of one of end portions of the X-ray beam on the reference cutting plane MA on a moving direction side of the X-ray tube 3 when the X-ray beam is irradiated from the X-ray tube 3 in the consecutive photographing start position is defined as an end side reference position k2.

According to one embodiment, extrapolation processing is performed on the area of the original image P0 shown by the hatched lines in FIG. 7. The hatched portion in FIG. 7 is an area where the range shown by the arrow in FIG. 7 is projected by an X-ray on the plane to which the detection plane of the FPD 4 belongs. Also in FIG. 8, extrapolation processing is performed on the hatched portion. The hatched portion in FIG. 8 is an area where the range shown by the arrow in FIG. 8 is projected by an X-ray on the plane to which the detection plane of the FPD 4 belongs.

The image processing section 12 in Example 1 is provided for the purpose of generating a tomographic image D controlled in image disturbance. For example, a series of original images P0 generated by the image generation section 11 is sent to the image processing section 12, and are subjected to various image processing by the image processing section 12 to be converted to a tomographic image D. Hereinafter, operations of the map generation section 12a, the extrapolation section 12b, and the tomographic image generation section 12c constituting the image processing section 12 will be explained.

<Operation of Map Generation Section>

The map generation section 12a performs gradation analysis on each original image P0 to calculate a gradient vector corresponding to a pixel constituting the original image P0. Then, gradient vectors are two-dimensionally arranged according to the corresponding pixels to generate a map "m." Therefore, the map "m" is generated for each of the original images P0.

Figure 9:
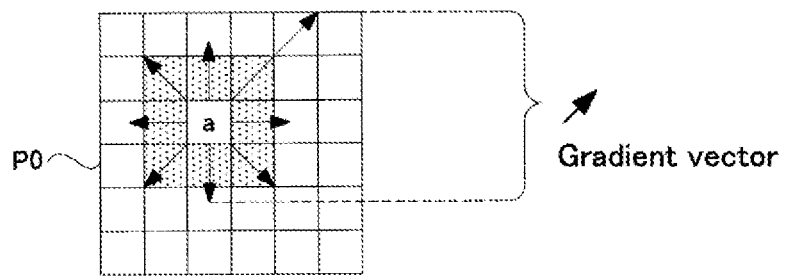
FIG. 9 is a schematic view for explaining the operation of a map generation section according to one exemplary embodiment.

FIG. 9 shows a general calculation method of a gradient vector. FIG. 9 shows a method of obtaining a gradient vector of a pixel "a" belonging to an original image P0. In order to obtain a gradient vector of the pixel "a," initially, a difference of pixel levels between the pixel "a" and each of peripheral pixels surrounding the pixel "a" is obtained. The peripheral pixels surrounding the pixel "a" include, as shown by the shading in FIG. 9, a total of 8 (eight) pixels arranged next to the left side, the right side, the upper side, the right obliquely upper side, the left obliquely upper side, the right obliquely lower side, and the left obliquely lower side of the pixel "a." As to each of the 8 (eight) peripheral pixels, the pixel level difference between the pixel "a" and each of the peripheral pixels is obtained. Then, a vector in which the pixel level corresponds to a length of the vector and the direction passing the pixel "a" and the peripheral pixel corresponds to a direction of the vector is generated on each of the 8 (eight) peripheral pixels. Then, as shown in FIG. 9, a total of 8 (eight) vectors extending from the pixel "a" in the left side direction, the right side direction, the lower side direction, the right obliquely upward direction, left obliquely upward direction, the right obliquely lower direction, and the left obliquely lower direction will be obtained. Then, these eight vectors are added to thereby obtain one vector. The obtained vector is a gradient vector for the pixel "a."

Figures 10A, 10B:
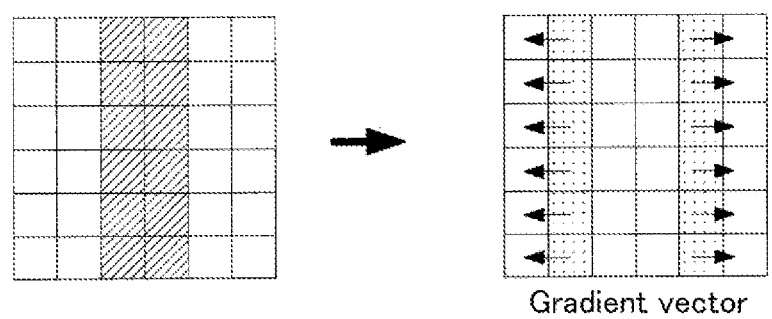
FIGS. 10A and 10B are schematic views for explaining the operation of the map generation section according to one exemplary embodiment.

The gradient vector shows the extending direction of the image to be seen in the original image P0. In detail, it is supposed that there is an image as shown in FIG. 10A. It is supposed that an image extending in the lengthwise direction is seen in the center of this image and the pixel level of the image is dark as compared with the periphery thereof. By performing a gradation analysis of this image and arranging the obtained gradient vectors in accordance with the positions of the pixels, a vector map as shown in FIG. 10B will be obtained. As such, a vector map in which gradient vectors each extending in the lateral direction at the shaded positions are arranged in the lengthwise direction can be obtained.

The gradient vector shows the direction along which the difference in pixel level between a certain pixel and its adjacent pixel and the magnitude of the difference of pixel values between a certain pixel and its adjacent pixel. Therefore, it can be concluded as follows from the gradient vector. An image extending in a direction perpendicular to the gradient vector exists in the original image, and the position of the image seen in the original image coincides with the position of the gradient vector in the vector map. The gradient vectors arranged in the vector map as mentioned above show the extending direction of a stripe-like structural object seen in the original image and the position of the object on the original image. Further, the length of the gradient vector shows how clearly the stripe-like structural object is seen.

Figure 11:
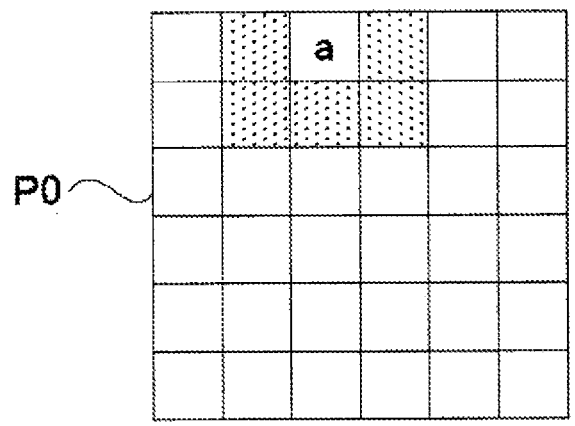
FIG. 11 is a schematic view for explaining the operation of the map generation section according to one exemplary embodiment.
Figure 12:
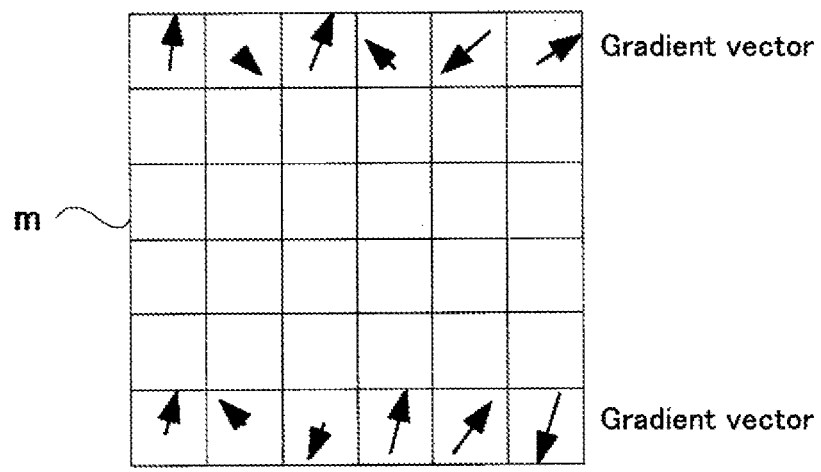
FIG. 12 is a schematic view for explaining the operation of the map generation section according to one exemplary embodiment.

The actual map generation section 12a performs a gradation analysis to the end section of the original image P0. Therefore, as shown in FIG. 11, the map generation section 12a obtains the gradient vector of a pixel "a" positioned on the end section of the original image P0 by using five peripheral pixels surrounding the pixel "a." Then, the map generation section 12a obtains gradient vectors of the pixel array of one row positioned on the end section of the original image P0, and further obtains gradient vectors of the pixel array of another row positioned on the side end portion opposite to the gradient vector obtained side. Then, the map generation section 12a generates a map "m" by arranging the obtained gradient vectors in accordance with the arrangement of the pixels in the original image P0. FIG. 12 shows a brief overview of the map "m." In the map "m" as shown in FIG. 12, on each of the pixels positioned on both end sections of the original image P0, a gradient vector corresponding to each pixel is mapped.

Both end sides of the original image P0 where the map generation section 12a obtains gradient vectors coincide with both end sections of the original image P0 in the moving directions of the X-ray tube 3 and the FPD 4.

<Operation of Extrapolation Section>

Figure 13:
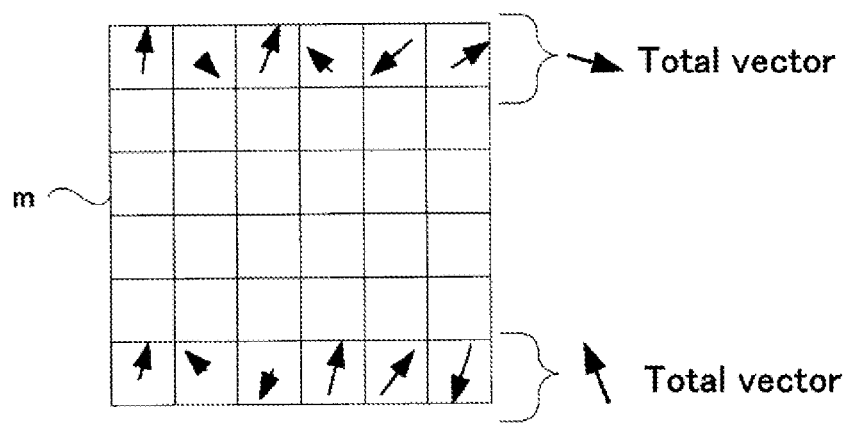
FIG. 13 is a schematic view for explaining the operation of the extrapolation section according to one exemplary embodiment.

The map "m" and its corresponding original image P0 are sent to the extrapolation section 12b. The extrapolation section 12b recognizes how the stripe-like structural object to be seen in the original image P0 extends at the end section of the original image by focusing attention on one row in which gradient vectors were obtained. As shown in FIG. 13, the extrapolation section 12b generates a single total vector by adding gradient vectors arranged in one row of the map "m." Further, the extrapolation section 12b generates a single total vector by adding gradient vectors arranged in another row of the map "m" in which gradient vectors were obtained.

Figures 14A, 14B:
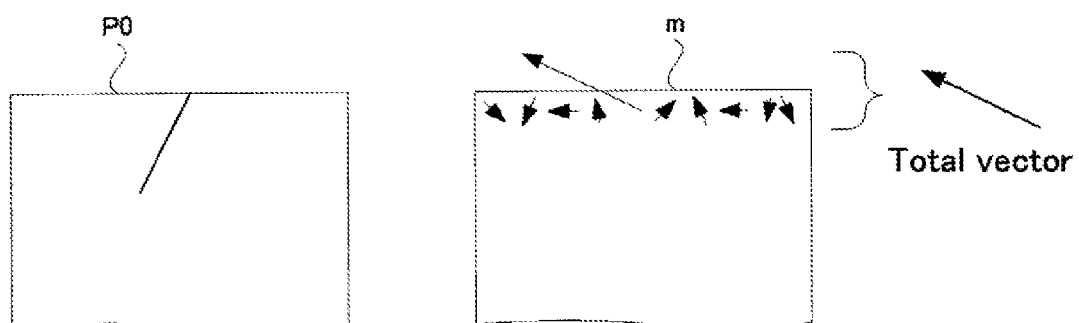
FIGS. 14A and 14B are schematic views for explaining the state in which a total vector is calculated according to one exemplary embodiment.

The meaning of the total vector will be explained. As shown in FIG. 14A, it is initially supposed that a linear structural object is seen in the end section of the original image P0. When generating a map "m" of the original image P0, the obtained map "m" is shown in FIG. 14B. In detail, a plurality of short gradient vectors pointed to various directions and a small number of long gradient vectors pointed in one direction are obtained. The reason will be explained below. In the portion where no structural object is seen in the original image P0, since similar pixels are arranged, the length of the gradient vector becomes short. In this portion, since noise is superimposed, the variation of pixel levels becomes irregular, the directions of the gradient vectors are irregular. On the other hand, in the map "m," at the position where the structure of the original image P0 is clearly seen, a gradient vector perpendicular to the extending direction of the structure is positioned. Further, the structure is clearly seen in the original image P0, and therefore the pixel level of the pixel belonging to the structure in the original image P0 differs from the pixel level of the peripheral pixels. Therefore, the length of the gradient vector becomes longer than that of the peripheral gradient vector.

FIG. 14B also shows a total vector which is a combination of these gradient vectors. According to this, the short vectors pointing to various directions are cancelled out, and the long gradient vector showing the extending direction of the structure is strongly seen in the total vector. For example, the total vector shows the extending direction of the linear structural object (e.g., exactly the direction perpendicular to the extending direction) in the original image P0.

Figures 15A, 15B:
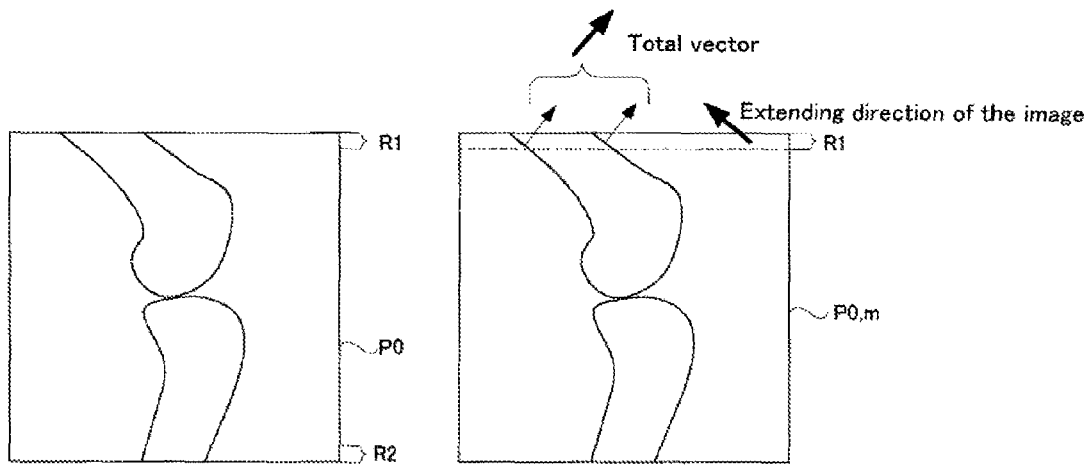
FIGS. 15A and 15B are schematic views for explaining the operation of the extrapolation section according to one exemplary embodiment.

FIG. 15A shows an example of an actually acquired original image P0 in which an image of a knee joint is seen. A pixel array R1 located at one side of the original image P0 is considered. In this pixel array R1, pixels are arranged on one line. FIG. 15B shows a state in which a map "m" corresponding to the original image P0 is superimposed on the original image P0. As will be understood from FIG. 15B, in the pixel array R1, long gradient vectors are seen at the contours of the thighbone. It should be noted that short vectors are omitted in FIG. 15B. The extrapolation section 12b combines these gradient vectors to obtain a total vector. Then, the extrapolation section 12b recognizes that the direction perpendicular to the total vector (the direction shown by a thick arrow in FIG. 15B) is the extending direction of the linear structural object seen in the end section of the original image P0.

Figure 16:
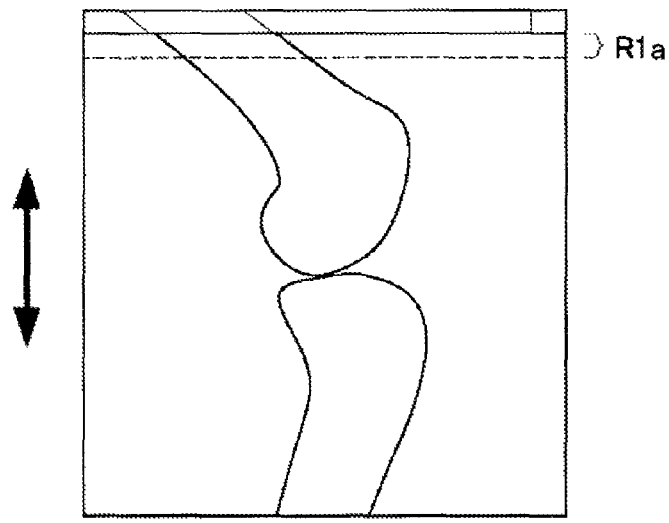
FIG. 16 is a schematic view for explaining the operation of the extrapolation section according to one exemplary embodiment.

FIG. 16 shows that the extrapolation section 12b extends the original image P0 by extrapolation. The extrapolation section 12b makes a duplication of the narrow area R1a of one side in which the total vector was calculated, and extends the original image P0 by adding the duplication to the one side of the original image P0 while shifting the duplication in the extending direction of the narrow are R1a. This shifting amount is obtained so that the duplication is accumulated in the direction perpendicular to the total vector. For example, when the total vector is perpendicular to the extending direction of the narrow area R1a, the extrapolation section 12b recognizes that the direction is the extending direction of the linear structural object to be seen in the narrow area R1a. And, the extrapolation section 12b adds the duplication to the original image as it is without shifting the duplication in the extending direction of the narrow area R1a.

Further, when the total vector is pointed in the right oblique direction as shown in FIG. 15B, the extrapolation section 12b recognizes that the linear structural object to be seen in the narrow area R1a extends in the left oblique direction perpendicular to the right oblique direction. The extrapolation section 12b adds the duplication to the original image P0 while shifting the duplication so that the linear structural object extends in the left oblique direction (see FIG. 16). For example, the extrapolation section 12b adds the duplication by adjusting the position of the duplication in the extending direction of the narrow area R1a so that the image of the subject seen in the end section of the original image P0 and the image of the subject seen in the duplication which is to be added are shifted in the left oblique direction (the direction perpendicular to the total vector). By doing this, the original image P0 is extrapolated while being extended in a state in which the linear structural object of the subject seen in the narrow area R1a is not discontinued and keeps the continuity. The duplication is added to the original image P0 while being shifted as mentioned above, and therefore the linear structural object seen in the narrow area R1a of the original image P0 is arranged in the extending direction in a state in which the linear structural object keeps the continuity.

Figure 17A:
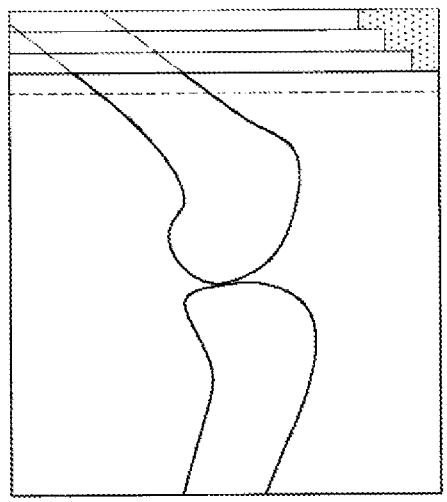
FIGS. 17A and 17B are schematic views for explaining the operation of the extrapolation section according to one exemplary embodiment.

FIG. 17A shows a state in which one side of the original image P0 is extended. At this time, the narrow area R1a is continuously arranged so as to be further added to the previously added narrow area R1a. By doing this, the extrapolation of the original image P0 is performed while extending the linear structural object seen in the original image P0. With this, the subject image of the original image P0 can be extrapolated in a continuous manner more naturally and seamlessly than the case in which the narrow area R1a is simply added without being shifted.

Now, how much the original image P0 is extended by the extrapolation will be explained. By adding the duplication of the narrow area R1a, the original image P0 extends in the lengthwise direction (moving direction of the imaging system 3 and 4) by the width of the narrow area R1a in the widthwise direction thereof. Since adding the duplication is repeatedly performed, the original image P0 extends by the width of the narrow area R1a in the widthwise direction thereof every time the duplication is added.

The number of adding the duplication of the narrow area R1a will be explained. The number of adding the duplication is decided based on the superimposing operation of images at the time of generating a tomographic image D. In one embodiment, the extrapolation section 12b continuously arranges the narrow area R1a of each original image P0 until it becomes a state (all extrapolated state) in which the subject image seen in an end section of one of 74 original images P0 is extrapolated in all other 73 original images P0. Thereafter, the extrapolation section 12b continues the extrapolation processing until all of 74 original images P0 become an extrapolated state.

For example, it is supposed that the photographing visual field moves in the original image P0 by one pixel when 74 original images are consecutively acquired. At this time, it can happen that the area of one pixel width arranged on the upper side of the initially acquired original image is not seen in the other 73 original images P0. This is because the photographing visual field is moved during the consecutive image acquiring operations. To compensate for the lack of the area, the extrapolation section 12b repeats the extrapolation processing to the 74 original images P0 to thereby generate an extrapolated image P1. For example, the extrapolation section 12b may continue the extrapolation processing until an area corresponding to the area is extrapolated in the other 73 original images P0.

For example, as to the secondary acquired original image P0, the extrapolation is performed on the upper side once. When the extrapolation processing is performed in the order of acquisition thereafter, the number of repetitions of the extrapolation processing to the original image P0 increases one by one. As for the last original image P0 acquired by the $74^{th}$ acquisition, 73 times extrapolation processing are performed on the upper side.

As to the lower side of the original image P0, the similar processing will be performed. For example, the area of one pixel width arranged on the lower side of the lastly acquired original image is not seen in the other 73 original images P0. The extrapolation section 12b continues the extrapolation processing until an area corresponding to the area is extrapolated in the other 73 original images P0. For example, as to the initially acquired original image P0, 73 times extrapolation processing is performed on the lower side. In the same manner, as to the original image P0 acquired at the $73^{rd}$ acquisition, only one time extrapolation processing is performed on the lower side.

The all extrapolated state in this example will be concretely explained. All extrapolated state of the $1^{st}$ acquired original image P0 is a state in which 73 times extrapolation processing to the lower side have been completed, and all extrapolated state of the $2^{nd}$ acquired original image P0 is a state in which one time extrapolation processing to the upper side and 72 times extrapolation processing to the lower side have been completed. Further, all extrapolated state of the 73$^{rd}$ acquired original image P0 is a state in which 72 times extrapolation processing to the upper side and one extrapolation processing to the lower side have been completed, and all extrapolated state of the lastly acquired original image P0 is a state in which 73 times extrapolation processing to the upper side have been completed. In the meantime, when the extrapolation section 12b performs one extrapolation processing, an extrapolation is performed in the lengthwise direction by one pixel width. As a result, the image extends in the lengthwise direction by one pixel. For example, the original images P0 are each extended in the lengthwise direction (moving direction) by 73 pixels, which generates an extrapolated image P1.

In general terms, the extrapolation processing is performed m−1 times in total. In accordance with this, the original image P0 is extended by n×(m−1), and an extrapolated image P1 is generated. In this example, "m" denotes the number of consecutive image acquisitions, and "n" denotes a moving amount showing how the photographing visual field moves on the original image P0 per one image acquisition during the consecutive photographing of the original image P0.

In the aforementioned operation, the range of the extrapolation can also be explained with the start side reference position k1 and the end side reference position k2 explained with reference to FIGS. 7 and 8. That is, the extrapolation section 12b obtains the start side reference position k1 and the end side reference position k2 on the reference cutting plane MA based on the positions of the X-ray tube 3 and the FPD 4 and the moving patterns of the X-ray tube 3 and the FPD 4. In the same manner, the extrapolation section 12b calculates where both end portions (the upper end and the lower end in FIG. 15 of the original image P0 in the moving direction of the X-ray tube 3 are positioned on the reference cutting plane MA. Then, the extrapolation section 12b repeats the extrapolation processing based on these calculated results. As such, as to the end portion (e.g., the upper end in FIG. 15) of the original image P0 in the direction opposite to the moving direction of the X-ray tube 3, the extrapolation section 12b performs extrapolation to the original image P0 up to the projection position of the start side reference position k1. In the same manner, as to the end portion (e.g., the lower end in FIG. 15) of the original image P0 in the moving direction of the X-ray tube 3, the extrapolation section 12b performs extrapolation to the original image P0 up to the projection position of the end side reference position k2.

Figure 17B:
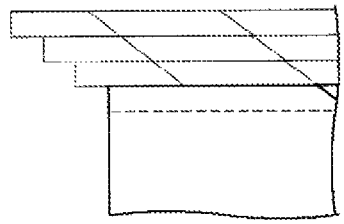

Further, when the narrow areas R1a are simply added, as shown in FIG. 17B, the narrow areas R1a protrude in a direction perpendicular to the image extending direction. To avoid such a problem, in one embodiment, the extrapolation section 12b trims the portions of the narrow areas protruded from the width of the original image P0. For example, the original image P0 may be shaped into a rectangular shape even after the extension.

The narrow area R1a can be the same area as the pixel array R1 which was used to search the linear structural object. The narrow area R1a can be a pixel array in which pixels are laterally arranged in line (in the direction perpendicular to the moving direction), and can have a thickness in the lengthwise direction (moving direction).

<Extraplation of Lacking Portion at Image Apex>

Next, an operation for which the extrapolation section 12b compensates a lack of image will be explained. In the portion of the apex section of the image shown by shading in FIG. 17A, no extrapolation is performed in the aforementioned arrangement operation. This is because this portion is an area which is not included in the narrow area R1a which is a duplication base. Therefore, after arranging the narrow areas R1a in the moving direction, the extrapolation section 12b externally inserts the shaded portion again using the narrow area R1a.

Figure 18A:
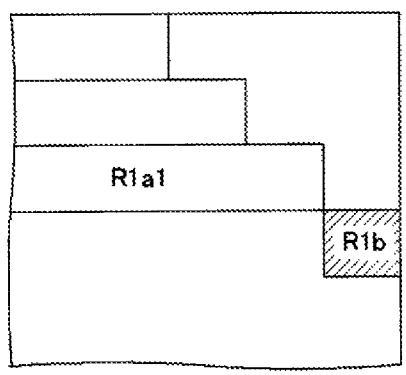
FIGS. 18A and 18B are schematic views for explaining the operation of the extrapolation section according to Example 1.
Figure 18B:
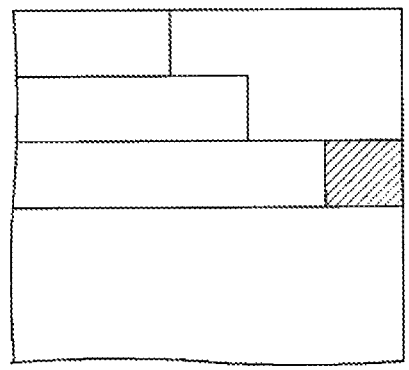

FIG. 18 shows the state in which the top section of the image is extrapolated. This explanation is directed to a case, as an example, in which the lack of image of the narrow area R1a1 in FIG. 18A is extrapolated. This narrow area R1a1 is one of duplications of the narrow area R1a arranged by the extrapolation processing of the extrapolation section 12b. The extrapolation section 12b adds the area R1b which is an area corresponding to the area which lacks in the narrow area R1a1 to the narrow area R1a1 in the direction perpendicular to the moving direction. This area R1b belongs to the narrow area R1a1. FIG. 18B shows a state in which a duplicate of the area R1b is arranged adjacent to the narrow area R1a1. The extrapolation section 12b repeats the similar operations to compensate for the lack of pixels occurring at the top portions of the image to thereby generate a rectangular image.

<About Side to which Extrapolation Section Performs Extrapolation Processing to Original Image>

Next, the explanation will be directed to the side to which the extrapolation section 12b performs the extrapolation processing to the original image P0. The extrapolation section 12b performs the extrapolation processing on the two sides parallel to each other among the four sides of the original image P0. These two sides extend in a direction perpendicular to the moving direction of the X-ray tube 3 and the FPD 4 shown by the arrow in FIG. 16. For example, the extrapolation section 12b operates to duplicate the strip-like pixel array at the side section extending in the orthogonal direction, which is a direction perpendicular to the moving direction, in the original image P0 and add the duplicate to the side section. In one embodiment, the extrapolation section 12b performs the similar operation not only to one side section of the original image P0 at the pixel array R1 side as shown in FIG. 15 but also to the side section of the original image P0 at the pixel array R2 side positioned on the side opposite to the pixel array R1. In the pixel array R2, pixels are arranged on one line. As explained above, the extrapolation section 12b performs image processing on both end sections of the original image P0 in the moving direction of the imaging system 3 and 4.

<About Smoothing Processing to be Performed by Extrapolation Section>

The extrapolation section 12b is not configured to simply duplicate the narrow area R1a and arrange it. The extrapolation section 12b performs smoothing processing to the narrow area R1a in the extending direction of the area (orthogonal direction perpendicular to the moving direction) and thereafter performs an adding operation. Further, this smoothing processing becomes stronger as the adding operation of the narrow area R1a is repeated. Therefore, when the duplication of the narrow area R1a added by the extrapolation section 12b is observed in turns from the center of the image to the end portion, blurring is gradually enhanced. In detail, the extrapolation section 12b gradually enhances the blurring degree of the smoothing processing to be performed to the narrow area R1a to be added as the adding operation of a plurality of narrow areas R1a is repeated.

The reasons for adding such a blurring operation will be explained below. As to the outside of the original image P0, there may not be any method to exactly know the state of the subject image. However, as to at least a portion adjacent to the end section of the original image P0 among the outside area, the portion should have the same pattern as the end section of the original image P0. Thus, as it moves away from the end section of the original image P0 among the outer area, it becomes difficult to predict the state of the subject image.

Even if narrow areas R1a are simply arranged without adding blurring, there should be no problem at the portion adjacent to the end section of the original image P0. However, thereafter, if narrow areas R1a are arranged continuously, the pattern of the image to be seen in the narrow area R1a becomes gradually different from the actual subject image. This is because the outer side portion of the image of the subject is not always the similar pattern as the narrow area R1a. In the extrapolated image P1 to be generated by the extrapolation section 12b, the outermost end section to which the extrapolation processing was performed becomes a pattern different from the original subject image. When a tomographic image D is generated using such an extrapolated image P1, a false image will be seen in the tomographic image D. This false image appears stronger as it reaches the outermost end portion of the tomographic image D. At the outermost portion of the tomographic image D, the difference between the actual subject image and the extrapolated image P1 may be severe, and this difference appears in the tomographic image D as a false image.

In order to solve such problems, the extrapolation section 12b adds a duplicate of the narrow area R1a to the original image P0 while performing the smoothing processing. Concretely, the smoothing processing is performed while increasing the degree of the smoothing processing every adding operation. By doing this, the duplicate of the narrow area R1a to be added becomes gradually unclear as it deviates from the original image P0. As a result, the image to be seen in the narrow area R1a, which becomes the cause of a false image, gradually becomes unclear, and therefore the false image to be seen in the tomographic image D will lose the sharpness. With this, it becomes possible to prevent that a false image is seen in the tomographic image D.

<Extrapolation Processing for Image in which Plural Linear Structural Objects are Seen>

The operation of the extrapolation section 12b as explained with reference to FIGS. 16 and 17 is directed to, for the convenience of the explanation, an extrapolation operation in the extending direction of the contour portion of a thighbone in an area on the map "m" corresponding to the pixel array R1. In the original image P0, various linear structural objects other than the contour portion of the thighbone are seen. The extending direction of this linear structural object does not always coincide with the extending direction of the contour of the thighbone. Therefore, even if the extrapolation section 12b performs the addition of an image based on the extending direction of the contour of the thighbone, the other linear structural object to be seen in the original image P0 is not always extended.

Figure 19A:
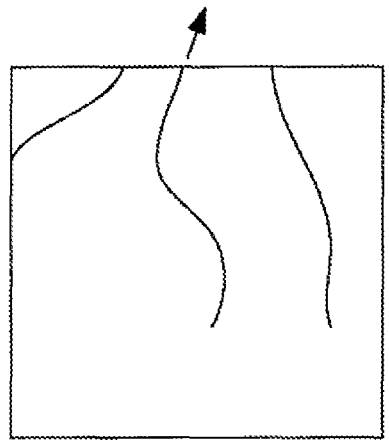
FIGS. 19A and 19B are schematic views for explaining the operation of the extrapolation section according to one exemplary embodiment.
Figure 19B:
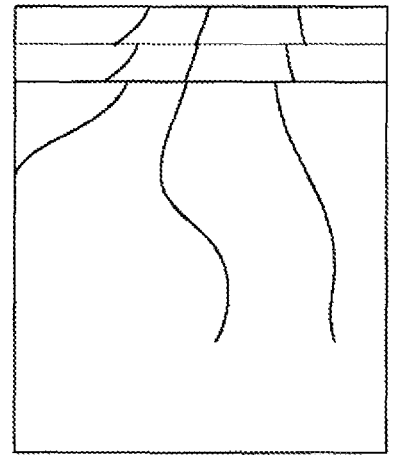

FIG. 19 illustrates this problem in a schematic way. Focusing on one of plural line structural objects seen in the original image in FIG. 19A, if images are added in the direction shown by the arrow, as shown in FIG. 19B, the focused linear structural object will be extended. However, the other linear structural objects seen in the image becomes discontinuous and intermittently positioned.

For this reason, the extrapolation section 12b performs extrapolation processing by dividing the narrow area R1a into a plurality of portions. In detail, in the extrapolation processing, the direction of adding an image to the original image P0 is changed depending on the portion of the image.

Figure 20:
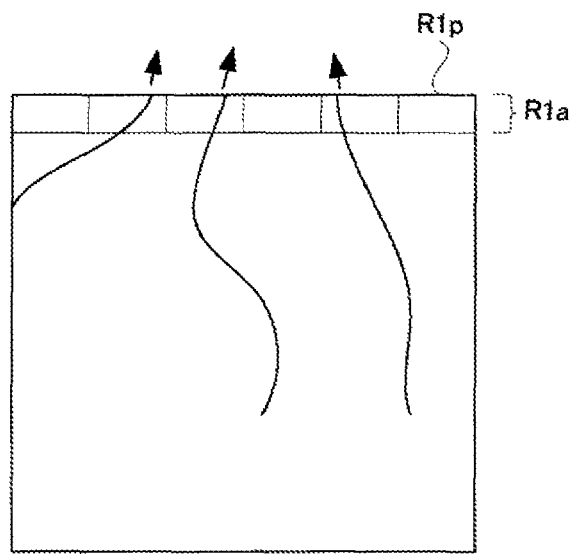
FIG. 20 is a schematic view for explaining the operation of the extrapolation section according to one exemplary embodiment.

FIG. 20 shows the state in which pieces of the divided narrow area R1a are joined separately. In FIG. 20, the narrow area R1a extending in the lateral direction is divided into the lateral direction at predetermined intervals. This divided piece will be shown by a symbol R1p. The extrapolation section 12b independently obtains a total vector on each of the pieces and calculates the extending direction of the linear structural object. Then, the extrapolation section 12b extends the image by adding the piece R1a in the lengthwise direction in FIG. 20 based on the extending direction of the image calculated every piece R1p. As a result, the image is extended by adding the duplicate of the piece R1p in the individual direction, which is different by each piece R1p, as shown by the arrow in FIG. 20.

At this time, a gap may be generated between the connected duplicates. In such a case, the extrapolation section 12b extrapolates the gap by duplicating a part of the piece R1p adjacent to a piece R1p and fitting the duplicate in the gap. The part of the piece R1p to be duplicated has the same size and shape as those of the gap.

The extrapolation section 12b performs the aforementioned operation about the pixel array R1 in the original image P0 and thereafter performs the same operation about the pixel array R2 in the original image P0 to thereby extend both sides of the original image P0 (see FIG. 15). The extrapolation section 12b performs the same extrapolation operation about all of the consecutively acquired original images P0 to generate a series of extrapolated images P1.

<Operation of Tomographic Image Generation Section>

The extrapolated image P1 is forwarded to the tomographic image generation section 12c. The tomographic image generation section 12c superimposes the series of extrapolated images P1 while shifting them in the moving direction of the X-ray tube 3 and the FPD 4 to generate a tomographic image D in which a tomographic image of the subject is seen at a predetermined cutting plane.

Further, the X-ray equipment 1 according to Example 1 is equipped with a main controller 25 for generally controlling each controller 6 and 8, and a display section 27 for displaying a tomographic image. This main controller 25 may be constituted by a CPU and executes various programs to realize each controller 6 and 8 and the below-mentioned each portion 11 and 12. In one embodiment, storage 23 stores all of parameters required for the control and image processing of the X-ray equipment 1. Further, the storage 23 may primarily store an intermediate image generated at the time of image processing.

<Operation of X-Ray Equipement>

Next, the operation of the X-ray equipment 1 will be explained. In order to obtain a tomographic image D using the X-ray equipment 1 according to Example 1, initially, a subject M is arranged on the top board 2. When an operator gives an instruction to acquire original images P0 via the console 26, the synchronous movement controller 8 moves the X-ray tube 3 and the FPD 4 to respective predetermined initial positions. At this time, the imaging system 3 and 4 is positioned as shown by the solid line in FIG. 2. In detail, the X-ray tube 3 at the initial position is positioned at the upstream side in the body axis direction A (longitudinal direction of the top board 2), and the FPD 4 is positioned at the downstream side in the body axis direction A. At this time, the X-ray tube 3 is tilted at the initial angle of −20 degree.

An X-ray tube controller 6 controls the X-ray tube 3, and the X-ray tube 3 irradiates an X-ray beam of a predetermined pulse width, tube voltage, and tube current toward the FPD 4. After passing through the top board 2, the X-ray beam enters the FPD 4. The image generation section 11 composes the detection signal output from the FPD 4 into an original image P0.

Thereafter, the synchronous movement controller 8 moves the X-ray tube 3 and the FPD 4 synchronously in opposite directions. The X-ray tube controller 6 controls to intermittently irradiate the X-ray beam during the movement, and the image generation section 11 generates original images P0 accordingly. Thus, a series of original images P0 are generated. At this time, the synchronous movement controller 8 moves the X-ray tube 3 toward the downstream side in the body axis direction A, and moves the FPD 4 toward the upstream side in the body axis direction A.

Then, the synchronous movement controller 8 moves the X-ray tube 3 and the FPD 4 to the respective predetermined final positions. The imaging system 3 and 4 at this time is arranged as shown by the alternate long and short dash line. For example, the X-ray tube 3 at the final position is positioned at the downstream side in the body axis direction A (longitudinal direction of the top board 2), and the FPD 4 at the final position is positioned at the upstream side in the body axis direction A. At this time, the X-ray tube 3 is tilted at a final angle of 20 degree. In this state, the last original image P0 is acquired, and obtaining a series of original images P0 is completed. In Example 1, 74 pieces of original images P0 are acquired.

The image processing section 12 generates a map "m" using the map generation section 12a every time an original image P0 is generated. The image processing section 12 performs extrapolation of the original image P0 using the extrapolation section 12b every time the map "m" is generated. An extrapolated image P1 generated as mentioned above becomes an image in which the original image P0 is extended in the moving direction of the imaging system 3 and 4.

The series of extrapolated images P1 generated as mentioned above generate a tomographic image D by the tomographic image generation section 12c of the image processing section 12. This tomographic image D is an image in which the tomographic image of the subject M suitable for diagnosis is seen. The tomographic image D is displayed on the display 27, and the operation terminates.

As explained above, the image processing apparatus according to the present disclosures initially creates a map "m" showing the extending direction of the linear structural object seen in the original image. Then, the image processing apparatus generates an extrapolated image P1 by adding the duplicate of the area positioned at the side section of the original image P0 to the side section of the original image P0 so that the linear structural object seen in the side section of the original image is arranged in the extending direction of the linear structural object. Further, this adding operation is performed to both side sections of the original image P0 in the moving direction of the X-ray tube 3 and the FPD 4. Thus, both side sections of the original image P0 in the moving direction are added so as to extend the linear structural object to thereby generate an extrapolated image P1. The portion deviated from the side section of the original image P0 is a portion that cannot be seen, and therefore it cannot be recognized the actual state of this portion of the original image P0. However, it is assumed that the image of the subject at the portion deviated from the original image P0 will continue for a while at least in the same pattern that the image of the side section of the original image P0 is extended.

Therefore, by adding the pattern of the side section of the original image P0 to the original image P0 while arbitrarily shifting the pattern in the extending direction of the side section so that the linear structural object seen in the side section of the original image is extended, it becomes possible to extrapolate the portion that cannot be seen on the image more naturally. That is, in the end portion of the generated extrapolated image P1, the subject image looks continuously extended. By generating the tomographic image D using such an extrapolated image P1, a tomographic image D excellent in visibility can be created.

The aforementioned structure shows a concrete structure of the extrapolation section 12b of the present disclosure. That is, when the adding operation by the extrapolation section 12b is performed by duplicating the strip-like pixel array positioned at the side section extending in the orthogonal direction perpendicular to the moving direction, it is more assuredly possible to generate an extrapolated image P1.

The aforementioned structure shows a concrete structure of the extrapolation section 12b of the present disclosure. That is, at the time of adding pixels, when the extrapolation section 12b performs smoothing processing on the strip-like pixel array in the orthogonal direction, a more clear tomographic image D can be obtained. It is expected that the transparent image of the subject of the outside section of the original image P0 is almost the same as the subject image seen in the side section of the original image P0. In actuality, however, the transparent image of the subject of the outside section of the original image P0 and the subject image seen in the side section of the original image P0 do not become exactly the same. Therefore, if the pixel is added as it is, a pattern different from the actual pattern will be added to the original image P0, resulting in an unnatural tomographic image D. According to the aforementioned structure, since smoothing processing is once performed and then the pixel is added, the unnaturalness of the tomographic image D becomes less noticeable, and the visibility of the tomographic image D improves.

The aforementioned structure shows a concrete structure of the extrapolation section 12b of the present disclosure. The prediction of the subject image not seen in the original image P0 becomes difficult as the predicting portion of the subject image deviates from the side section of the original image P0. For example, in the outside area of the original image P0, the part of the transparent image of the subject adjacent to the side section of the original image P0 is almost the same as the subject image seen in the side section. However, in the outside area of the original image P0, the image of the subject becomes different from the subject image seen in the side section. According to certain embodiments of the present invention, as the operation of adding a plurality of pixel arrays repeats, the blurring degree of the smoothing processing to be performed to the pixel array to be added is gradually enhanced. With this, it is possible to avoid the possibility that patterns which gradually differ from the original subject image are added as the adding operation is repeated.

The aforementioned structure shows a structure of the radiation tomography apparatus mounting the image processing apparatus according to one embodiment of the present invention. According to the radiation tomography apparatus of the present disclosed embodiments, a tomographic image D improved in visibility of both ends of the tomographic image D can be obtained.

The present invention is not limited to the aforementioned structure, and can be modified, for example, as explained below.

(1) In the aforementioned structure, although the total vector is obtained from the pixel array R1 in which pixels positioned at the end section of the original image P0 are arrayed on a line, the present invention is not limited to this structure. For example, the total vector can be obtained using an area increased in the width in the widthwise direction in place of the pixel array R1.

(2) In the aforementioned structure, although the image extrapolation processing is performed by obtaining the total vector on each of a plurality of divided pieces of the pixel array R1, the present invention is not limited to this structure. For example, the extrapolation processing can be performed based on the profile about the length of the gradient vector.

Figure 21A:
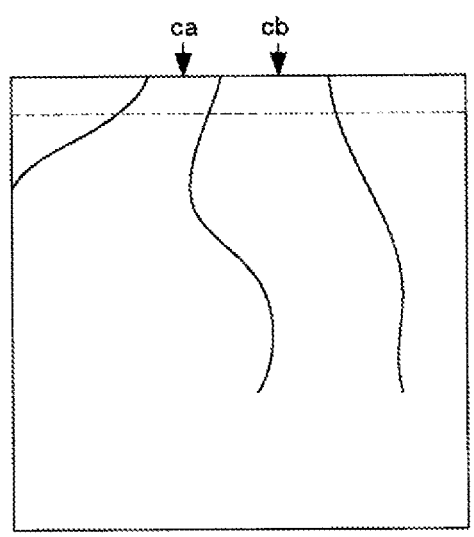
FIGS. 21A and 21B are schematic views for explaining one modified exemplary embodiment of the present invention.
Figure 21B:
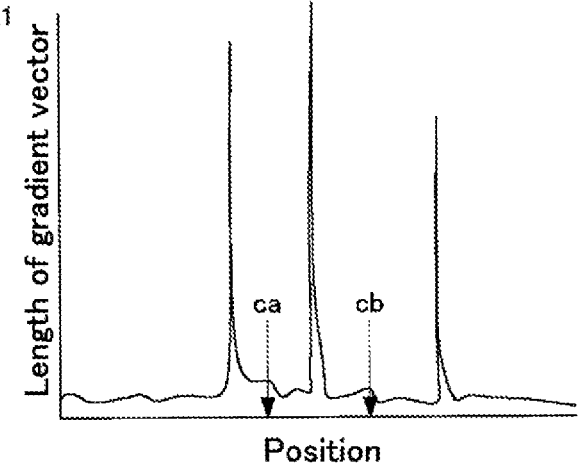
Figure 22:
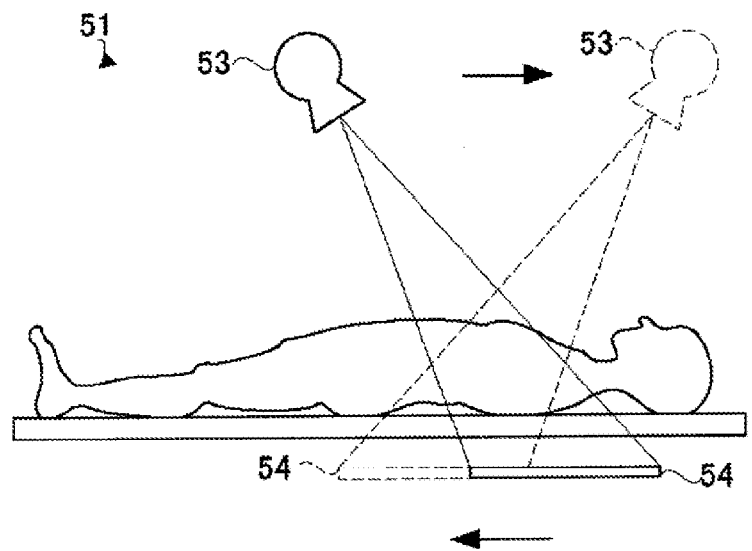
FIG. 22 is a schematic view for explaining a structure of a conventional X-ray tomographic apparatus.
Figure 23:
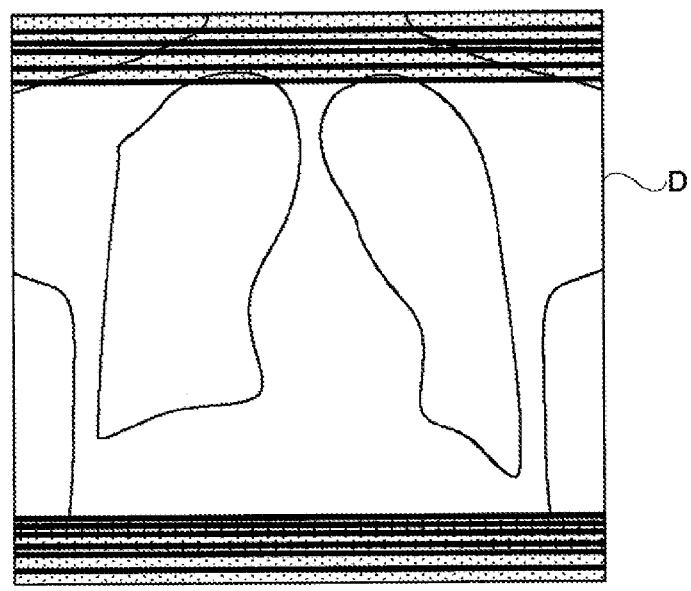
FIG. 23 is a schematic view for explaining a structure of a conventional X-ray tomographic apparatus.
Figure 24:
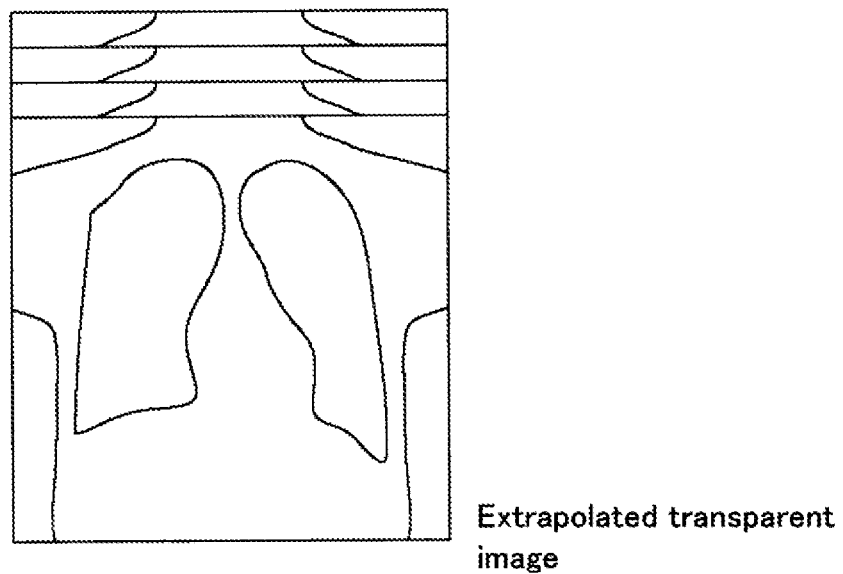
FIG. 24 is a schematic view for explaining certain problems of a conventional X-ray tomographic apparatus.

This modified example will be explained concretely. FIG. 21A shows an example in which a plurality of linear structural objects are seen in the side section of the original image P0. The map generation section 12a obtains gradient vectors on this original image P0 and arranges the gradient vectors to generate a map "m." Based on this map "m," the extrapolation section 12b generates a profile in which the position on the image and the magnitude of the gradient vector are related. In this profile, as shown in FIG. 21B, three peaks appear. The extrapolation section 12b recognizes these three peaks to know that the linear structural object is positioned on which portion in the side section of the original image P0. The peak is judged whether or not the value of the maximum part in the profile exceeds a predetermined threshold. When the value of the maximum part is equal to or larger than the threshold, the extrapolation section 12b judges this maximum part as a peak to initiate the operation.

The extrapolation section 12b divides the pixel array R1 depending on the positions where peaks appear and operates. In detail, the extrapolation section 12b obtains an intermediate point between adjacent two peaks on the profile and divides the pixel array R1 at the position shown by the intermediate point. In the example shown in FIG. 21, since three peaks appear, two intermediate points ca and cb, between the adjacent first peak and second peak, and between the adjacent second peak and third peak, are set. The extrapolation section 12b obtains a total vector on each of three sections, e.g., a section from the left end of the pixel array R1 on the original image P0 to the intermediate point ca, a section from the intermediate point ca to the intermediate point cb, and a section from the intermediate point cb to the right end, performs extrapolation section on the original image P0 every section. With this, each of linear structural objects on the original image P0 is extended in the extending direction, and the original image P0 is extrapolated. By this, a tomographic image D with less disturbed image can be obtained. As the method of determining the intermediate point, a position sandwiched by adjacent two peaks can be an intermediate point, and it is more preferable that the intermediate point is defined as a position with the same distance from two peaks.

The entire disclosure of Japanese Patent Application No. 2012-043369 filed on Feb. 19, 2012, which describes certain features related to the present disclosure, is incorporated herein by reference in its entirety.

The terms and descriptions used herein are used only for explanatory purposes and the present invention is not limited to them. Accordingly, the present invention allows various design-changes falling within the claimed scope of the present invention.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, the terminology "present invention" or "invention" is meant as a non-specific, general reference and may be used as a reference to one or more aspects within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

What is claimed is:

1. An image processing apparatus comprising:
a map generation block configured to generate a gradient vector map by calculating gradient vectors showing an extending direction of a linear structural object seen in a series of images consecutively acquired while moving a radiation source for irradiating an X-ray to a subject and a radiation detection means for detecting the X-ray passed through the subject synchronously in opposite directions and arranging the vectors;
an extrapolation block configured to generate a series of extrapolated images by adding a duplicate of an area positioned at a side section of the images to the side section of the images so that the linear structural object seen in the side section of the images is arranged in the extending direction of the linear structural object; and
a tomographic image generation block configured to generate a tomographic image by superimposing the extrapolated images,
wherein the extrapolation block is configured to perform image processing to both end sections of the images in a direction in which the radiation source and the radiation detection means move.

2. The image processing apparatus as recited in claim 1, wherein the extrapolation block is configured to duplicate a strip-like pixel array positioned at the side section extending in an orthogonal direction perpendicular to a moving direction in the image and add the duplicate to the side section.

3. The image processing apparatus as recited in claim 2, wherein the extrapolation block is configured to perform smoothing processing of the strip-like pixel array in the orthogonal direction when adding the pixel array.

4. The image processing apparatus as recited in claim 3, wherein the extrapolation block is configured to gradually increase a degree of blurring of the smoothing processing to be performed to the pixel array to be added as an operation for adding a plurality of the pixel arrays repeats.

5. The image processing apparatus as recited in claim 1, wherein the extrapolation block is configured to generate a total vector by adding the gradient vectors arranged in the gradient vector map and add the duplicate to the side section of the image based on the total vector.

6. The image processing apparatus as recited in claim 5, wherein the extrapolation block is configured to compensate an area adjacent to the duplicate caused by adding the duplicate while shifting with a part of the duplicate.

7. The image processing apparatus as recited in claim 1, wherein the extrapolation block is further configured to add the duplicate to the duplicate previously added to the side section of the image.

8. The image processing apparatus as recited in claim 1, wherein the extrapolation block is configured to divide the duplicate into a plurality of divided pieces and add the divided pieces to the side of the image.

9. The image processing apparatus as recited in claim 8, wherein the extrapolation block is configured to add the plurality of divided pieces to the side of the image while shifting in individual directions.

10. The image processing apparatus as recited in claim 9, wherein the extrapolation block is configured to obtain a total vector on each of the plurality of divided pieces by adding the gradient vectors and add the divided pieces to the side of the image while shifting in individual directions based on a direction of the total vector.

11. A radiation tomography apparatus mounting the image processing apparatus as recited in claim 1, comprising:
 a radiation source configured to irradiate radiation to a subject;
 a radiation detector configured to detect the radiation passed through the subject;
 a moving mechanism configured to move the radiation source and the radiation detection means synchronously in a moving direction in opposite directions with respect to the subject;
 a movement controller configured to control the moving mechanism; and
 an image generation block configured to generate the image based on an output of the radiation detector.

12. The radiation tomography apparatus as recited in claim 11, wherein the extrapolation block is configured to operate to duplicate a strip-like pixel array positioned at the side section of the image extending in an orthogonal direction perpendicular to a moving direction of the radiation source and the radiation section and add the duplicate to the side section.

13. The radiation tomography apparatus as recited in claim 12, wherein the extrapolation block is configured to perform smoothing processing of the strip-like pixel array in the orthogonal direction when adding the pixel array.

14. The radiation tomography apparatus as recited in claim 13, wherein the extrapolation block is configured to gradually increase a degree of blurring of the smoothing processing to be performed to the pixel array to be added as an operation for adding a plurality of the pixel arrays repeats.

15. The radiation tomography apparatus as recited in claim 11, wherein the extrapolation block is configured to generate a total vector by adding the gradient vectors arranged in the gradient vector map and adds the duplicate to the side section of the image based on the total vector.

16. An image processing apparatus comprising:
 map generation means for generating a gradient vector map by calculating gradient vectors showing an extending direction of a linear structural object seen in a series of images consecutively acquired while moving a radiation source for irradiating an X-ray to a subject and a radiation detection means for detecting the X-ray passed through the subject synchronously in opposite directions and arranging the vectors;
 extrapolation means for generating a series of extrapolated images by adding a duplicate of an area positioned at a side section of the images to the side section of the images so that the linear structural object seen in the side section of the images is arranged in the extending direction of the linear structural object; and
 tomographic image generation means for generating a tomographic image by superimposing the extrapolated images,
 wherein the extrapolation means are configured to perform image processing on both end sections of the images in a direction in which the radiation source and the radiation detection means move.

17. A method of performing image processing comprising:
 generating a gradient vector map by calculating gradient vectors showing an extending direction of a linear structural object seen in a series of images consecutively acquired while moving a radiation source for irradiating an X-ray to a subject and a radiation detection means for detecting the X-ray passed through the subject synchronously in opposite directions and arranging the vectors;
 generating a series of extrapolated images by adding a duplicate of an area positioned at a side section of the images to the side section of the images so that the linear structural object seen in the side section of the images is arranged in the extending direction of the linear structural object; and
 generating a tomographic image by superimposing the extrapolated images,
 wherein image processing is performed on both end sections of the images in a direction in which the radiation source and the radiation detection means move.

18. The method as recited in claim 17, further comprising:
 duplicating a strip-like pixel array positioned at the side section extending in an orthogonal direction perpendicular to a moving direction in the image and adding the duplicate to the side section.

19. The method as recited in claim 18, further comprising:
 performing smoothing processing of the strip-like pixel array in the orthogonal direction when adding the pixel array.

20. The method as recited in claim 19, further comprising:
 gradually increasing a degree of blurring of the smoothing processing to be performed to the pixel array to be added as an operation for adding a plurality of the pixel arrays repeats.

* * * * *